US009072431B2

(12) United States Patent
Adams et al.

(10) Patent No.: US 9,072,431 B2
(45) Date of Patent: Jul. 7, 2015

(54) ACCESS SYSTEM WITH REMOVABLE OUTFLOW CHANNEL

(75) Inventors: Ronald David Adams, Holliston, MA (US); Eric Karl Litscher, Hopkinton, MA (US)

(73) Assignee: HOLOGIC, INC., Bedford, MA (US)

( * ) Notice: Subject to any disclaimer, the term of this patent is extended or adjusted under 35 U.S.C. 154(b) by 1033 days.

(21) Appl. No.: 13/179,430

(22) Filed: Jul. 8, 2011

(65) Prior Publication Data

US 2012/0010464 A1    Jan. 12, 2012

Related U.S. Application Data

(63) Continuation of application No. 12/956,974, filed on Nov. 30, 2010, now abandoned, which is a continuation of application No. PCT/US2010/056416, filed on Nov. 11, 2010.

(60) Provisional application No. 61/261,289, filed on Nov. 13, 2009.

(51) Int. Cl.
*A61B 1/00* (2006.01)
*A61B 1/015* (2006.01)
(Continued)

(52) U.S. Cl.
CPC .............. *A61B 1/015* (2013.01); *A61B 1/303* (2013.01); *A61B 17/32002* (2013.01); *A61B 17/3462* (2013.01)

(58) Field of Classification Search
CPC ........... A61B 1/00094; A61B 1/00119; A61B 1/303; A61B 1/307
USPC ......... 600/104, 105, 135, 138, 153, 154, 156, 600/204
See application file for complete search history.

(56) References Cited

U.S. PATENT DOCUMENTS 4,673,393 A   6/1987  Suzuki et al.
4,895,565 A   1/1990  Hillstead
(Continued)

FOREIGN PATENT DOCUMENTS

EP    2498668    9/2012
WO    99/11184   3/1999

OTHER PUBLICATIONS

PCT International Search Report and the Written Opinion of the International Searching Authority for PCT/US2010/056416, dated Jan. 11, 2011 (9 pages).
(Continued)

*Primary Examiner* — Anhtuan T Nguyen
*Assistant Examiner* — Timothy J Neal
(74) *Attorney, Agent, or Firm* — Vista IP Law Group LLP

(57) ABSTRACT

A surgical access device can comprise a working channel providing a first lumen having an axial opening for insertion of a surgical instrument having an outflow channel, the first lumen having a fluid inlet for allowing fluid flow through the working channel and into the body, wherein fluid flows out of the body through the outflow channel of the surgical instrument; and a optical channel providing a second lumen for a visualization element and a light source, wherein the working channel comprises a larger cross-sectional area than the cross-sectional area of the optical channel. The surgical access device can further comprise a seal apparatus coupled to the working channel and configured to receive the surgical instrument, the seal apparatus comprising a first seal portion and a second seal portion, the first seal portion configured to close the fluid path into the seal apparatus, and the second seal portion configured to form a seal with the surgical instrument.

14 Claims, 17 Drawing Sheets

(51) Int. Cl.
*A61B 1/303* (2006.01)
*A61B 1/12* (2006.01)
*A61B 17/32* (2006.01)
*A61B 17/34* (2006.01)

(56) References Cited

U.S. PATENT DOCUMENTS

| | | | |
|---|---|---|---|
| 4,998,527 | A | 3/1991 | Meyer |
| 5,125,903 | A | 6/1992 | McLaughlin et al. |
| 5,320,091 | A | 6/1994 | Grossi et al. |
| 5,392,765 | A | 2/1995 | Muller |
| 5,503,626 | A | 4/1996 | Goldrath |
| 5,618,296 | A | 4/1997 | Sorensen et al. |
| 5,624,395 | A | 4/1997 | Mikhail et al. |
| 5,709,664 | A | 1/1998 | Vandenbroek et al. |
| 5,843,046 | A | 12/1998 | Motsi et al. |
| 5,916,198 | A | 6/1999 | Dillow |
| 6,086,544 | A | 7/2000 | Hibner et al. |
| 6,117,070 | A | 9/2000 | Akiba |
| 6,126,635 | A | 10/2000 | Simpson et al. |
| 6,149,632 | A | 11/2000 | Landuyt |
| 6,682,477 | B2 | 1/2004 | Boebel et al. |
| 7,150,713 | B2 | 12/2006 | Shener et al. |
| 7,497,833 | B2 | 3/2009 | Miller |
| 7,588,545 | B2 | 9/2009 | Cohen et al. |
| 7,749,254 | B2 | 7/2010 | Sobelman et al. |
| 7,785,250 | B2 | 8/2010 | Nakao |
| 7,938,804 | B2 | 5/2011 | Fischvogt |
| 2001/0047183 | A1 | 11/2001 | Privitera et al. |
| 2001/0056222 | A1* | 12/2001 | Rudischhauser et al. ..... 600/130 |
| 2004/0204682 | A1 | 10/2004 | Smith |
| 2005/0085692 | A1 | 4/2005 | Kiehn |
| 2006/0047185 | A1 | 3/2006 | Shener et al. |
| 2007/0161957 | A1 | 7/2007 | Guenther et al. |
| 2007/0232859 | A1 | 10/2007 | Secrest et al. |
| 2007/0238928 | A1 | 10/2007 | Maseda |
| 2008/0058595 | A1 | 3/2008 | Snoke et al. |
| 2008/0091074 | A1* | 4/2008 | Kumar et al. ................. 600/156 |
| 2008/0147012 | A1 | 6/2008 | Rome |
| 2008/0249366 | A1 | 10/2008 | Gruber et al. |
| 2008/0249553 | A1 | 10/2008 | Gruber et al. |
| 2009/0005739 | A1 | 1/2009 | Hart et al. |
| 2009/0054728 | A1 | 2/2009 | Trusty |
| 2009/0137927 | A1 | 5/2009 | Miller |
| 2009/0198149 | A1 | 8/2009 | Privitera et al. |
| 2009/0270898 | A1 | 10/2009 | Chin |
| 2010/0063360 | A1 | 3/2010 | Harrington et al. |
| 2010/0152533 | A1 | 6/2010 | Mark |
| 2010/0152761 | A1 | 6/2010 | Mark |
| 2010/0179480 | A1 | 7/2010 | Sugiki et al. |
| 2010/0185153 | A1 | 7/2010 | Sugiki et al. |
| 2010/0274194 | A1 | 10/2010 | Sobelman et al. |
| 2010/0312053 | A1 | 12/2010 | Larsen |

OTHER PUBLICATIONS

Extended European Search Report for EP Pub. No. 2498668, EP Application No. 10830744.8, dated Jul. 9, 2013 (8 pages).
"The Intra Uterine Morcellator: A New hysteroscopic operating technique to remove intrauterine polyps and myomas," Mark Hans Emanuel and Kees Wamsteker, Journal of Minimally Invasive Gynecology (Jan./Feb. 2005) vol. 12, No. 1, 62-66, (5 pages).

* cited by examiner

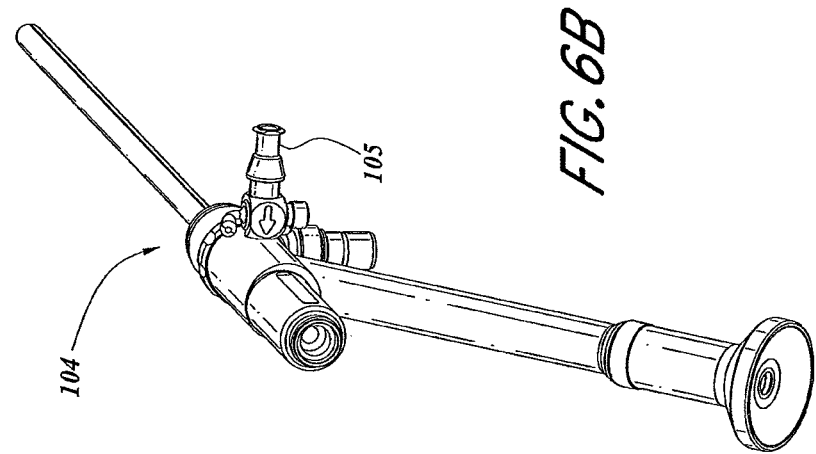
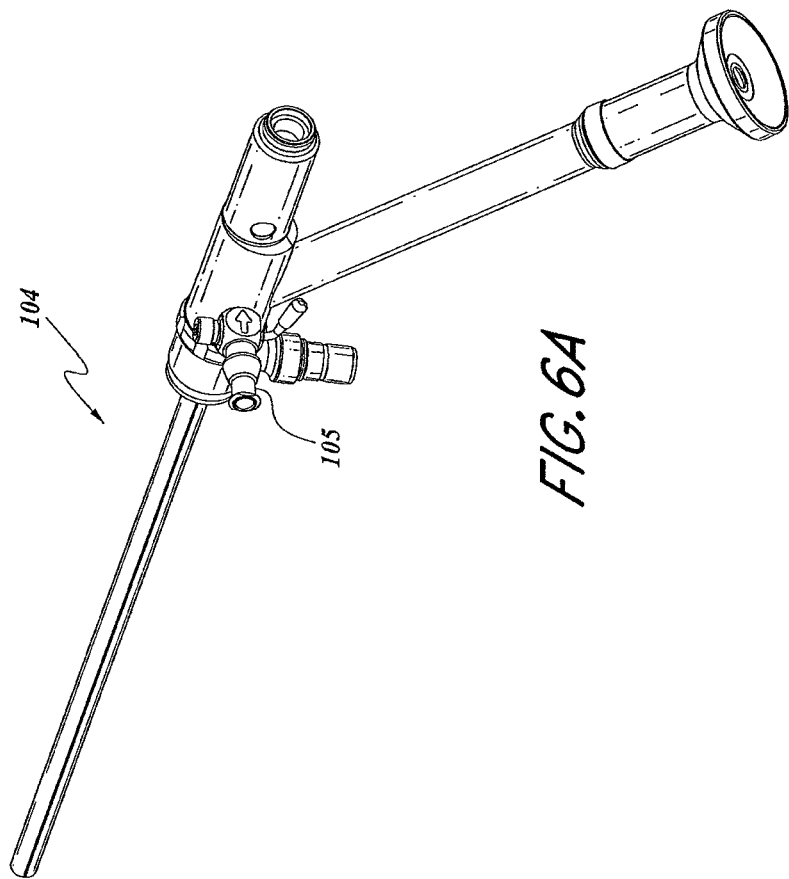

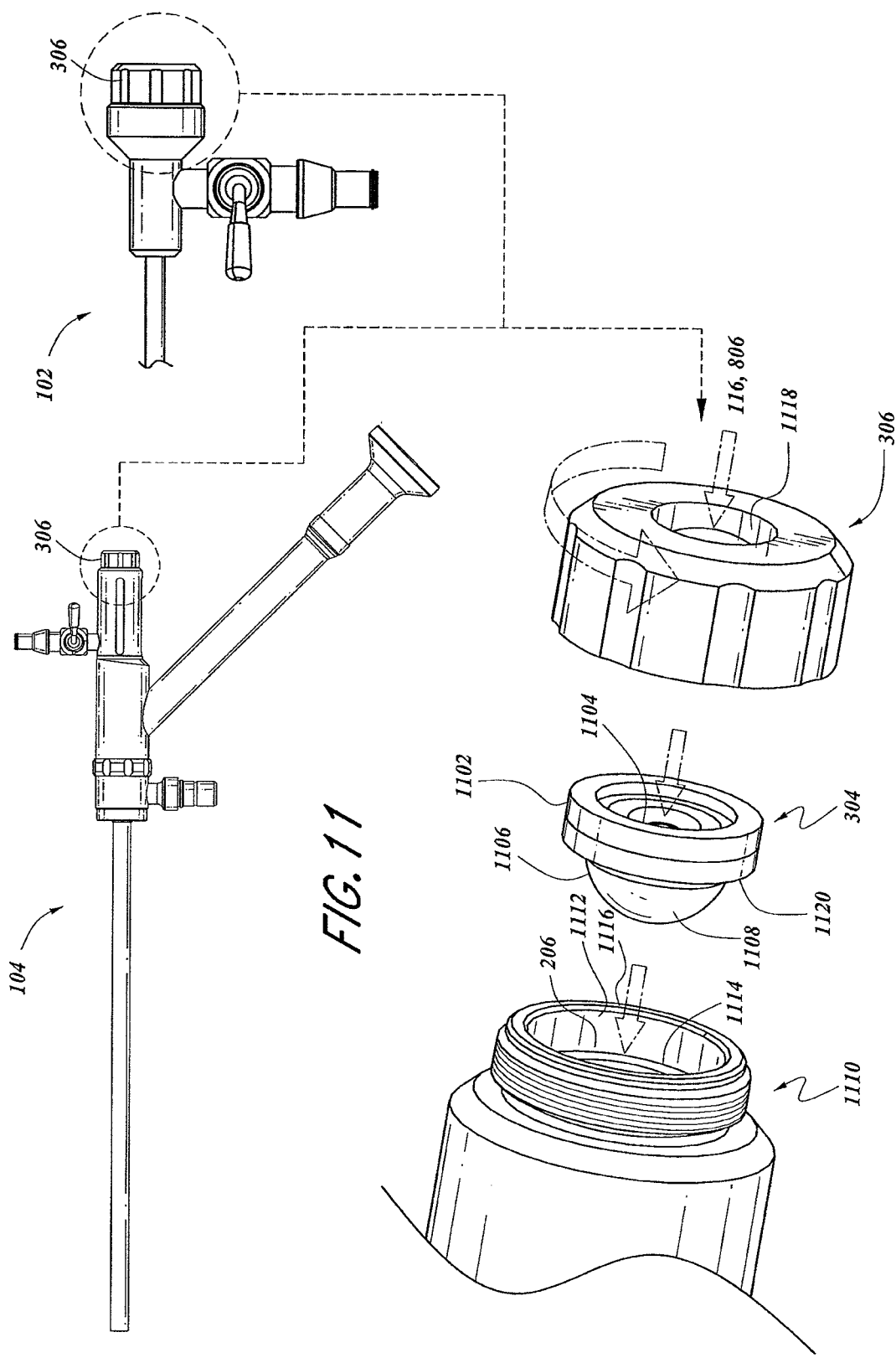

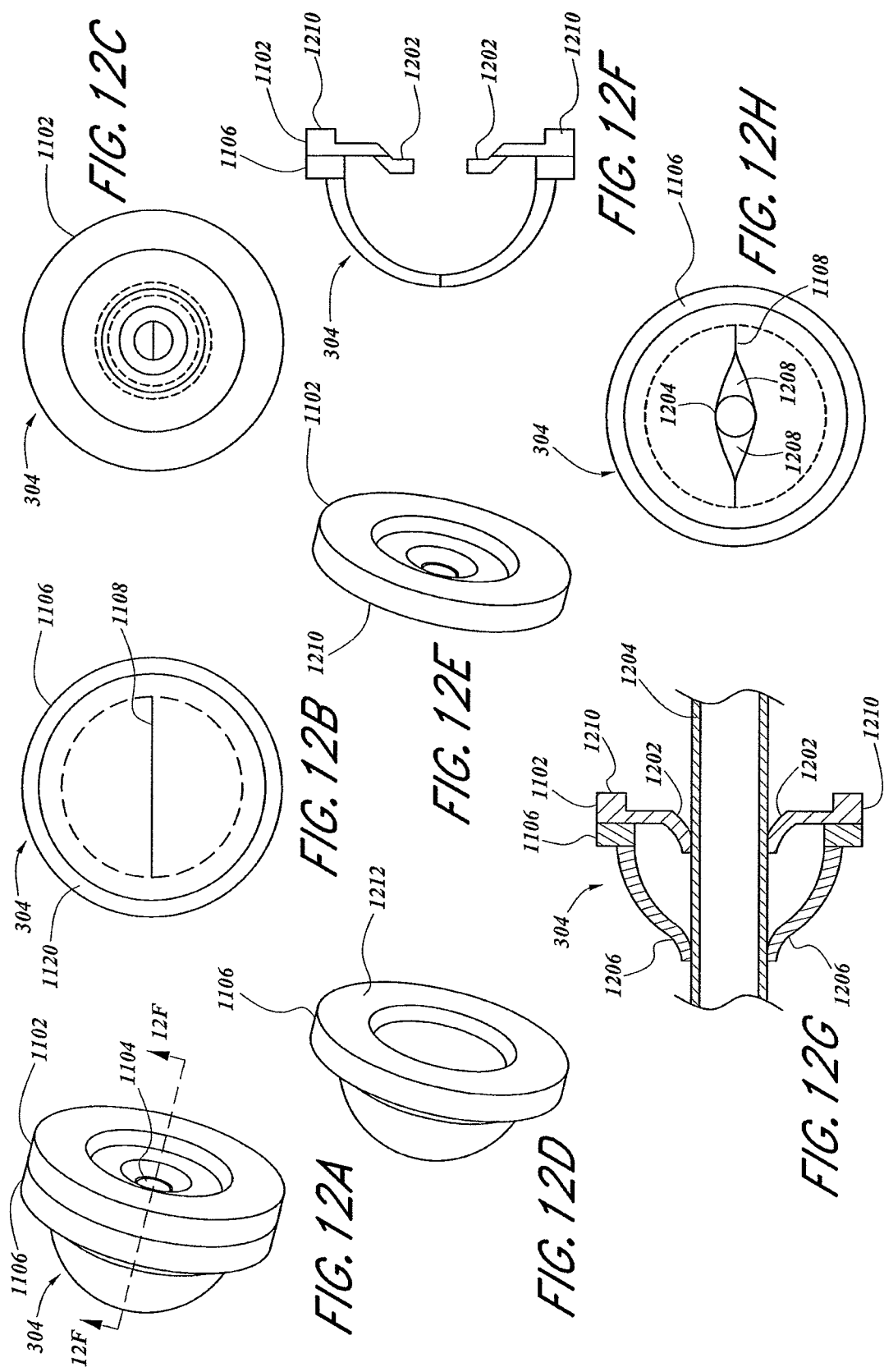

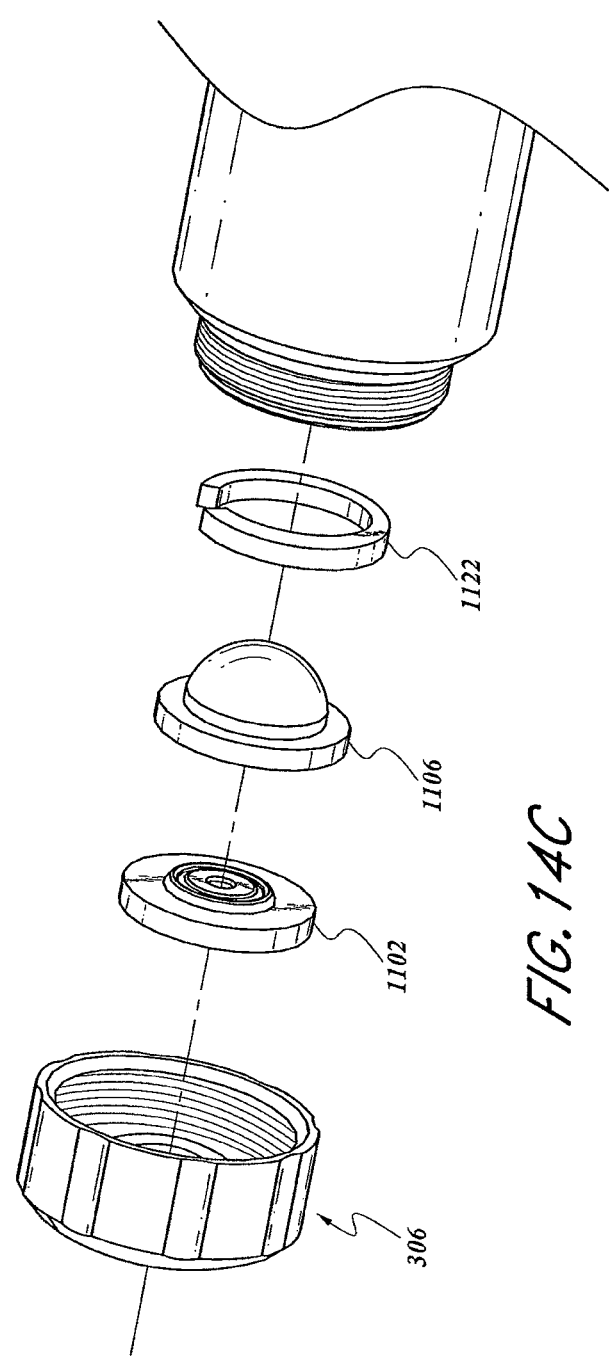

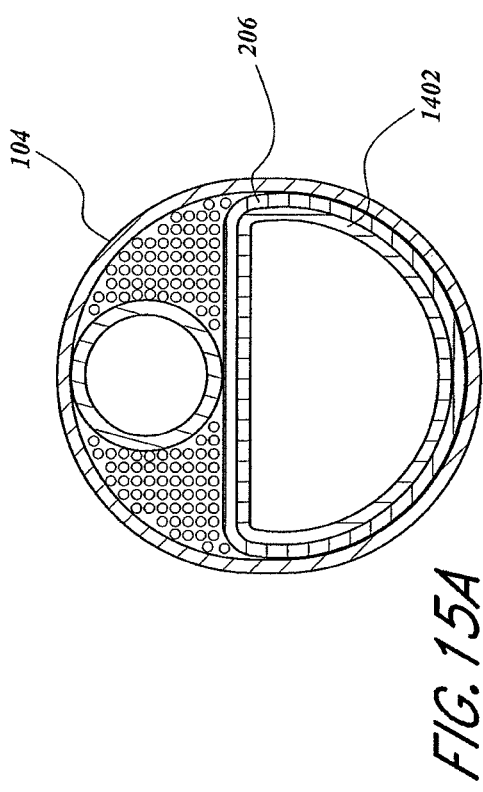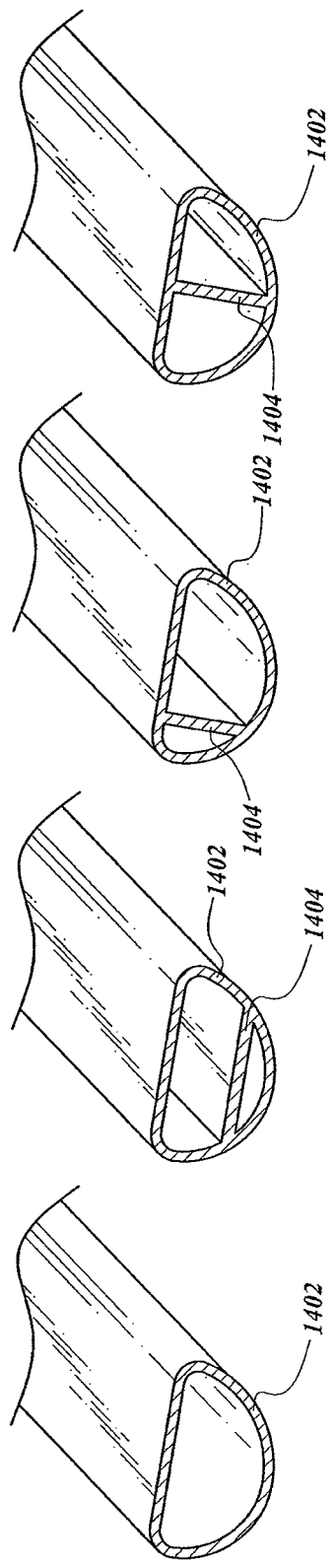

ACCESS SYSTEM WITH REMOVABLE OUTFLOW CHANNEL

CROSS-REFERENCE TO RELATED APPLICATIONS

This application is a continuation of U.S. application Ser. No. 12/956,974, filed on Nov. 30, 2010 and titled ACCESS SYSTEM WITH REMOVABLE OUTFLOW CHANNEL, which is a continuation of PCT Application No. PCT/US2010/056416, filed on Nov. 11, 2010 and titled ACCESS SYSTEM WITH REMOVABLE OUTFLOW CHANNEL, which claims the benefit of U.S. Provisional Application No. 61/261,289, titled ACCESS SYSTEM WITH REMOVABLE OUTFLOW CHANNEL and filed on Nov. 13, 2009. The foregoing applications are hereby incorporated by reference herein in their entirety as disclosed therein.

BACKGROUND

1. Field

The present inventions relate generally to methods, systems, and devices for surgical procedures, such as endoscopic surgical procedures.

2. Description of the Related Art

Surgeons typically use various devices for analyzing, diagnosing, and/or removing tissue from the body. In some circumstances, the subject tissue is easily accessible by surgeons and can be analyzed and/or removed without causing significant discomfort, injury, or trauma to the patient. In other instances, the subject tissue is difficult to access because, for example, of body orifice restrictions (e.g., diameter, rigidity, or the like).

Uterine fibroids and other abnormal gynecological tissues are examples of tissues that are difficult to access. It is believed that uterine fibroids occur in a substantial percentage of the female population, perhaps in at least 20 to 40 percent of all women. Generally, uterine fibroids can be well-defined, non-cancerous tumors that can be commonly found in the smooth muscle layer of the uterus. In many instances, uterine fibroids can grow to be several centimeters in diameter and may cause symptoms like menorrhagia (prolonged or heavy menstrual bleeding), pelvic pressure or pain, and reproductive dysfunction.

Difficulties in accessing the uterus have been the subject of various journal articles. For example, the Journal of Lower Genital Tract Disease, by the American Society for Colposcopy and Cervical Pathology, published an article, titled, "Overcoming the Challenging Cervix Techniques to Access the Uterine Cavity." The article discusses various challenges for accessing the uterus and cites that: "One study reported that 47% of failed outpatient hysteroscopy procedures are because of cervical stenosis and undue pain during negotiation of the endocervical canal." Conventional devices, modalities, and treatments for accessing the uterus can cause much discomfort, injury and/or trauma to the patient.

BRIEF DESCRIPTION OF THE DRAWINGS

The foregoing and other features, aspects and advantages of the embodiments of the inventions disclosed herein are described in detail below with reference to the drawings of various embodiments, which are intended to illustrate and not to limit the inventions. The drawings comprise the following figures in which:

FIGS. 6A-6B are proximal perspective views of the access device illustrated in FIG. 1.

FIG. 11 is a top, proximal, and side perspective and exploded view of the removable outflow channel illustrated in FIG. 1 having a seal apparatus.

FIG. 12A is a proximal, bottom, and side perspective view of the seal apparatus illustrated in FIG. 11.

FIG. 12B is a distal elevational view of the seal apparatus illustrated in FIG. 11.

FIG. 12C is a proximal elevational view of the seal apparatus illustrated in FIG. 11.

FIG. 12D is a proximal, bottom, and side perspective view of a dome-seal portion of the seal apparatus illustrated in FIG. 11.

FIG. 12E is a proximal, bottom, and side perspective view of a circular-seal portion of the seal apparatus illustrated in FIG. 11.

FIG. 12F is a cross-sectional view of the seal apparatus illustrated in FIG. 11.

FIG. 12G is a cross-sectional view of the seal apparatus having an instrument inserted through the seal apparatus.

FIG. 12H is a distal view of the seal apparatus having an instrument inserted through the seal apparatus.

FIGS. 14B-14C are partial exploded views of two embodiments of the seal apparatus for the access device.

FIG. 15A a cross-sectional view of a rod and/or shaft of the access device illustrated in FIG. 1.

FIGS. 15B-15E are top, side perspective views of various embodiments of sheaths for insertion into the access device.

DETAILED DESCRIPTION OF THE EMBODIMENTS

Although several embodiments, examples and illustrations are disclosed below, it will be understood by those of ordinary skill in the art that the invention described herein extends beyond the specifically disclosed embodiments, examples and illustrations and includes other uses of the invention and obvious modifications and equivalents thereof. Embodiments of the invention are described with reference to the accompanying figures, wherein like numerals refer to like elements throughout. The terminology used in the description presented herein is not intended to be interpreted in any limited or restrictive manner simply because it is being used in conjunction with a detailed description of some specific embodiments of the invention. In addition, embodiments of the invention can comprise several novel features and no single feature is solely responsible for its desirable attributes or is essential to practicing the inventions herein described.

The various embodiments of the present invention provide novel methods, systems and devices for tissue access, diagnosis, and/or removal. The methods, systems and devices are disclosed in the context of hysteroscopes and methods utilizing hysteroscopes because they have particular utility in this context. The inventions disclosed herein, however, can also be used in other contexts, such as, for example, but without limitation, inspection tools, tools for machining, devices including slidable fluid seals, as well as other contexts.

Figure 1:
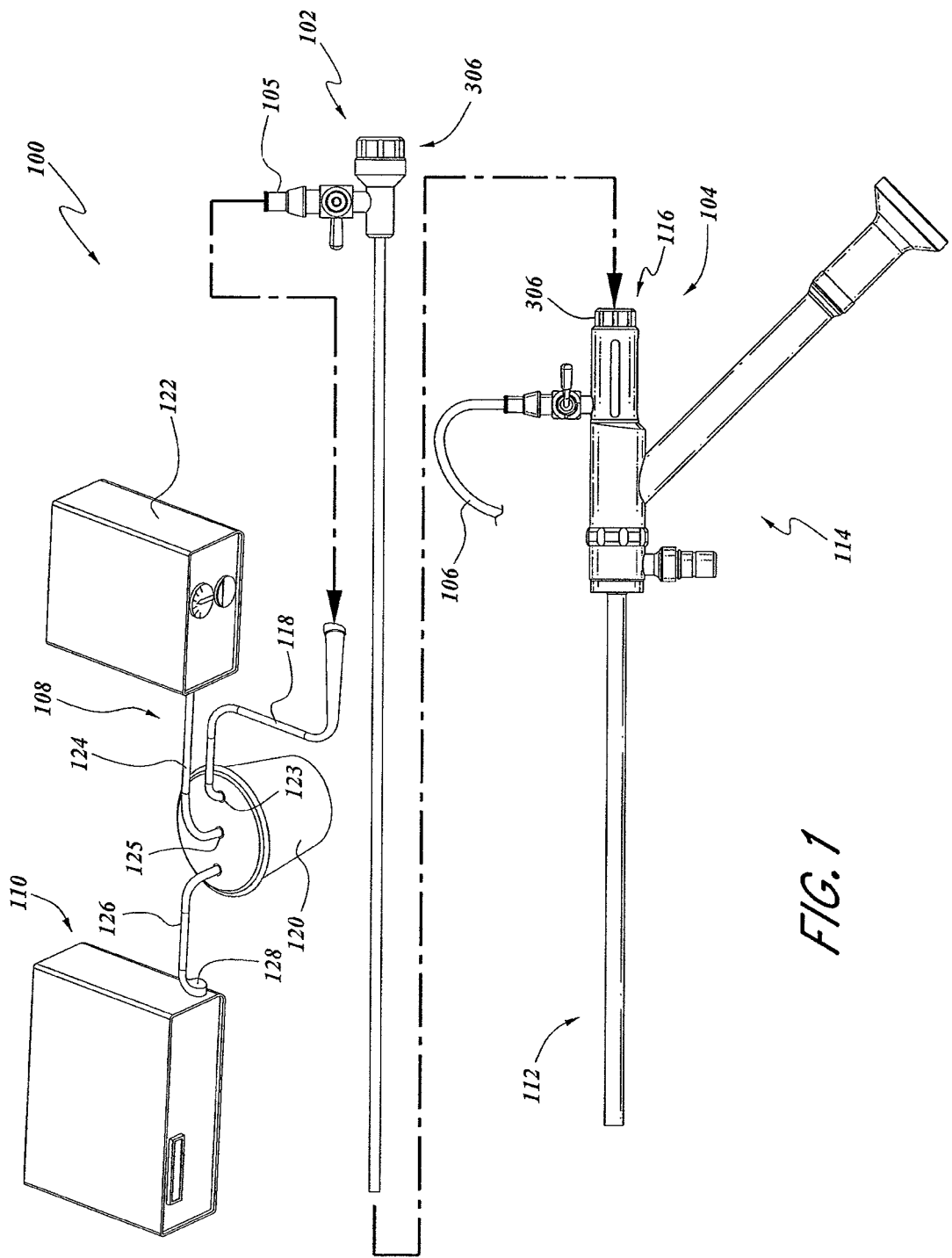
FIG. 1 is a partially exploded and schematic view of an embodiment of a surgical access system, including an access device and a removable outflow channel.

FIG. 1 schematically illustrates a surgical access and tissue removal system 100. In this case, the access device has been selected to illustrate the principles of the embodiments; however, it will be understood that such principles apply equally to all types of surgical access devices, as well as to devices not necessarily limited to surgical access. Generally, the embodiments disclosed herein encompass devices comprising a working channel or other types of lumens where it is desirable to provide simultaneous inflow and outflow of fluid while receiving various surgical instruments through the working channel or lumen. Such devices can include, without limitation, hysteroscopes, endoscopes, catheters, cannulas, and the like. Thus, although the embodiments described with respect to an access device intended for gynecological procedures is illustrative only and not intended to be limiting in any respect.

In the case of gynecological procedures there is a particular need for a working channel having simultaneous inflow and outflow of fluid while allowing for various surgical instruments to be inserted and retracted through the working channel. This configuration allows the access device to have a small cross-sectional profile and/or a slim profile, which can minimize discomfort, trauma, and/or injury to the patient during a gynecological procedure. For example, if the access device is entering the cervix, then an access device having a smaller cross-sectional profile will cause less pain to the patient as the access device is inserted into the cervix. A smaller profile will likely require little to no cervical dilation. By combining the working channel with the inflow and outflow channels, as opposed to having separate and/or distinct channels for each, the profile or the cross-sectional area or diameter of the access device can be reduced.

Additionally, a smaller profile can also allow surgeons to make smaller incisions for the access device to enter, thereby allowing patients to suffer reduced trauma, and/or to experience minimized scarring, and/or to heal faster. Further, by consolidating the working channel with the inflow and outflow channels, additional space can be devoted to the working channel, thereby allowing the working channel to be sufficiently large to receive a wide variety of surgical instruments, for example, diagnostic instruments and/or tissue removal devices (for example, morcellators). Accordingly, surgeons need only insert a single access device into a patient as opposed to inserting a first access device for performing a diagnostic procedure, and then removing the first access device and inserting a second larger access device for performing a surgical procedure, for example, surgical removal of tissue.

With further reference to FIG. 1, the surgical access and tissue removal system 100, in the illustrated embodiment, can be considered a surgical access system 100 configured for gynecological procedures, such as hysteroscopy, cystoscopy, arthroscopy; however, a wide variety of procedures may be performed with the surgical access system 100. In addition to the performance of one or more gynecological procedures described in detail herein, the systems, methods, apparatuses, and devices disclosed herein can be used to perform one or more additional procedures (for example, urological procedures or the like), including but not limited to access and tissue manipulation and/or tissue removal from any of a variety of organs and tissues, such as the bladder, breast, lung, stomach, bowel, esophagus, oral cavity, rectum, nasal sinus, Eustachian tubes, heart, gall bladder, spine, shoulder, knee, hip, brain, arteries, veins, and various ducts. Routes of access include but are not limited to trans-cervical; trans-vaginal-wall; trans-uteral; trans-vesicle; trans-urethral; and other routes.

The surgical access and tissue removal system 100 can comprise an access device 104 and a removable outflow channel 102. The surgical access system 100 can further comprise a fluid supply 106, and a vacuum assembly 108. In some embodiments, the surgical access system can comprise an electrical hardware assembly 110.

As illustrated in FIG. 1, the access device 104 can comprise a distal insertion portion 112, which is intended for insertion into the patient's body, and a proximal portion 114, which generally remains outside the patient's body. In this case, the access device 104 can be referred to as a hysteroscope, wherein access to the patient's body is achieved through the cervix; however, the access device 104 can be a wide variety of other instruments, for example, endoscopes, catheters, cannulas, and the like, and in other procedures, access may be gained through other natural openings or orifices in the body (for example, ears nose, mouth, via trans-rectal, urethral, vaginal approach, or the like), or through surgical incision, or the like. The details of the distal insertion portion 112 are described below in connection with FIGS. 2A-2C, while the details of the proximal portion 114 are described below in connection with FIG. 2D.

Above the access device 104 in FIG. 1, there is illustrated in exploded relationship to the access device 104, a removable outflow channel 102. The removable outflow channel 102 can be inserted into the access device 104 through a proximal entry opening or port 116. The insertion of the removable outflow channel 102 into the access device 104 is merely illustrative, and a wide variety of other instruments can be used in connection with the proximal entry port 116.

For example, a tissue manipulation and/or removal device, such as a tissue removal device 1002 as described below and illustrated in FIG. 10, and as further described in U.S. patent application Ser. No. 12/432,647, titled "ACCESS DEVICE WITH ENHANCED WORKING CHANNEL," which is hereby incorporated by reference in its entity, can also be used in connection with the proximal entry port 116. The proximal entry port 116 can comprise a seal apparatus 304 (described below in connection with FIGS. 11-13D). In some embodiments, the removable outflow flow channel 102 is inserted through the proximal entry port 116 and/or through the seal apparatus 304, and into the lumen of the access device 104.

Above the outflow channel 102 in FIG. 1, there is illustrated a vacuum assembly 108 and an electrical hardware assembly 110. The vacuum assembly 108 can be connected to the removable outflow channel 102 through a outflow tube 118. Outflow tube 118 can be connected to a specimen collection container 120. A vacuum source 122 can be connected to specimen collection container 120 through a tube 124. The electrical hardware assembly 110 may be connected to the specimen container 120 through a tube 126. The electrical hardware assembly 110 may comprise a vacuum sensor 128 that can be coupled to the tube 126 for monitoring the pressure within container 120.

Access Device and Removable Outflow Channel

FIGS. 2A-2D illustrate the access device 104 inserted with the removable outflow channel 102. This combination can be used for diagnostic use; however, this combination can be utilized for other uses.

Figure 2:
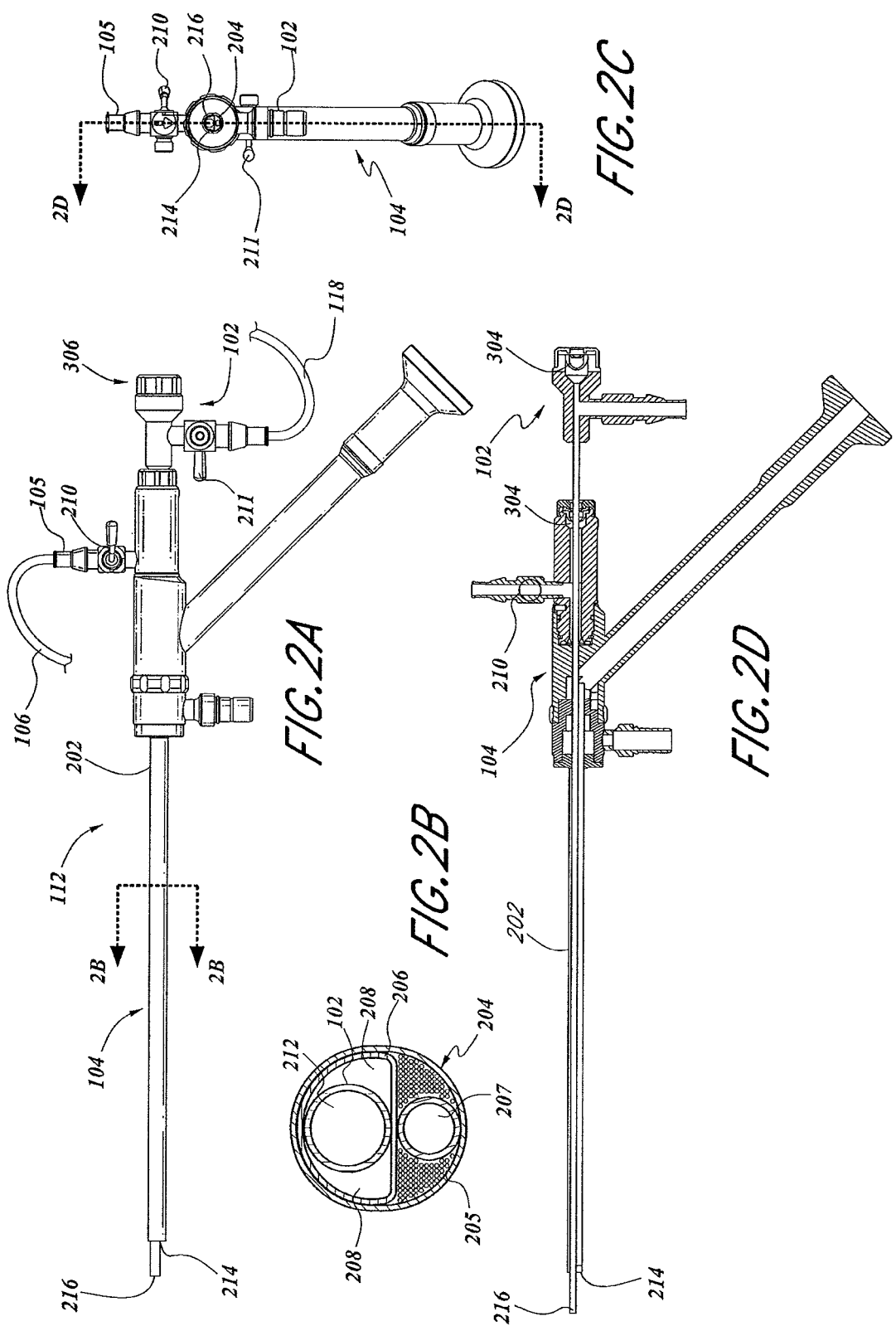
FIG. 2A is a side elevational view of the access device and the removable outflow channel devices illustrated in FIG. 1, wherein the outflow channel is positioned within the access device.
FIG. 2B is a cross-sectional view of the access device and the removable outflow channel devices illustrated in FIG. 2A, taken along line 2B-2B.
FIG. 2C is a distal elevational view of the access device and the removable outflow channel devices illustrated in FIG. 2A.
FIG. 2D is a longitudinal cross-sectional view of the access device and the removable outflow channel devices illustrated in FIG. 2A.

The hysteroscope 104 can comprise a distal portion 112 having a straight rigid rod and/or shaft 202 for insertion into the patient's vaginal opening and through the cervix to access the uterine cavity; however, in some embodiments, the distal portion 112 is flexible and/or semi-flexible. A cross-sectional view of the rigid rod and/or shaft 202 is illustrated in FIG. 2B. In some embodiments, the rigid rod and/or shaft 202 comprises an optical system and/or visualization element 207 and a working channel 206. The working channel 206 is configured to receive the removable outflow channel 102; however, a wide variety of surgical instruments may be inserted into the working channel 206. In some embodiments, the working channel can be configured to have area of 14.1 mm sq. It should be noted that the ratio of the area of the instrument lumen 102 to working channel 206 can exceed 50% (e.g. 53.5%) illustrating the challenge of balancing the inflow area 208 and the outflow area 212 when optimizing the overall system performance.

The area within the working channel and surrounding the removable outflow channel 102 can also act as a fluid inflow conduit 208, which is in fluid communication with fluid inlet port 105 that connects to the fluid supply 106 (for example, distension fluid). The fluid supply can comprise a peristaltic pump, a fluid-containing syringe, or other suitable fluid-dispensing device, with or without an automated mechanism from dispensing inflow fluid at a desired rate and/or pressure. In some embodiments, the fluid supply 106 can include a pressure sensor configured to detect a pressure of the fluid discharged from the pump or in the inflow conduit 208. Such a pressure sensor can be used to limit the pressure of the fluid discharged from the pump and for estimating a pressure within a body cavity into which the shaft 202 is inserted.

A surgeon using the hysteroscope 104 for a surgical procedure can open, close, and/or limit the amount of fluid flowing into the fluid inflow conduit 208 and into the patient's body, here the uterine cavity, by adjusting the inflow fluid stopcock 210. The area within the removable outflow channel acts as a fluid outflow conduit 212, which is in fluid communication with the outflow tube 118. The surgeon may open, close, and/or limit the amount of fluid flowing through the fluid outflow conduit 212 and out of the patient's body, here the uterine cavity, by adjusting the outflow fluid stopcock 211. In operation, fluid from fluid supply 106 passes through inflow fluid stopcock 210 and flows through fluid inflow conduit 208 and out distal inflow fluid opening 214. Fluid in the body, in this case the uterine cavity, enters distal outflow fluid opening 216 and flows through fluid outflow conduit 212 of the removable outflow channel 102, and passes through outflow fluid stopcock 211. While outflow fluid is flowing through the fluid outflow conduit 212, a surgeon may insert and retract a wide variety of surgical instruments through the removable outflow channel 102.

Alternatively, it is preferable in some situations to allow outflow tube 118 to be terminated into a drainage basin or drape wherein the inflow pressure drives the fluid outflow at a reduced rate.

Access Device

With reference to FIGS. 3A-3D, the access device 104 can comprise a shaft 202, and in some embodiments, the shaft 202 can be rigid, and can be constructed from a wide variety of materials. Such materials can include without limitation stainless steel (for example, SAE grade 316 or 304), polymers, plastics, or the like. As illustrated in FIG. 3B, the shaft 202 can comprise an outer portion 301 having an inner working channel 206 welded, bonded, or otherwise coupled to the outer portion 301. In some embodiments, the outer portion 301 and the working channel 206 can be constructed from a die casting process using molds to shape the molten metal (or other material) into a desired configuration. In some embodiments, the outer portion 301 and the working channel 206 can be constructed from a single sheet of material (for example, a metal alloy such as stainless steel) that is formed to construct the working channel, and then rolled into a substantially circular shape to form the outer portion 301, wherein the joints are welded together. In some embodiments, the shaft is flexible and/or semi-flexible, and can be constructed from a wide variety of materials including without limitation polymers, plastics, or the like. Depending on the materials used for construction, the access device 104 can be configured to be reusable (and sterilize-able), and/or disposable for one-time use. In some embodiments, parts and/or portions of the access device 104 are reusable while other parts and/or portions are disposable. For example, the shaft 202 and/or the access device body 316 can be reusable (and sterilize-able), while the light post 310 and/or the introduction section 314 and/or the seal apparatus 304 can be disposable for one time use.

The rod or shaft 202 of the access device of 104 can be dimensioned to enter a wide variety of natural body orifices and/or surgical sites and/or incisions. In the case of gynecological procedures wherein the rigid shaft 202 enters the cervix, the shaft 202 can have a diameter of 6.25 mm to minimize pain, discomfort, and/or injury to the patient while maximizing the cross-sectional area of the shaft 202. A 6.25 mm diameter size will generally require local anesthesia because substantial dilation of the cervix may not be required; however, the access device can be configured with shafts 202 having other diameter sizes, for example, 2 mm, 3 mm, 4 mm, 5 mm, 6 mm, 7 mm, 8 mm, 9 mm, 10 mm, 11 mm, and 12 mm, and preferably between 5 mm-8 mm to minimize patient discomfort and/or injury while maximizing the cross-sectional area of the shaft.

In some embodiments, the cross-sectional shape of the shaft 202 is substantially oval and/or elliptical to provide the working channel a greater cross-sectional area and/or to allow the shaft 202 to pass more easily through the body orifice and/or the surgical site/incision. As illustrated in FIG. 3B, the transverse diameter of the elliptically shaped shaft 202 extends between the top and bottom portions 300a, 300b of the shaft 202 to provide for a "taller" shaft profile. For example, the shaft 202 can be configured to be 6.4 mm tall and 6 mm wide. In some embodiments, the height to width ratio can be 1.07 to 1; however, other ratios are possible. In some embodiments, the transverse diameter extends between the sides of the shaft 202 to provide for a "wider" shaft profile. In some embodiments, the cross-sectional shape of the shaft 202 is substantially circular; however, a wide variety of other shapes are possible, for example, a rounded rectangular shape.

The access device 104 can comprise a working channel 206 and an optical system and/or a visualization element 207, within an optical channel 205, for inspecting and viewing the surgical site, in this case, a uterine cavity. In some embodiments, the working channel 206 and the optical channel 205 have substantially "D" shaped or semi-circle cross-sectional areas. To provide greater area for allowing surgical instruments, fluids, and the like to pass through the working channel, the cross-sectional area of the working channel can be greater than the optical channel by a ratio of 2:1, 1.5:1, 1.2:1 or by some other ratio. In some embodiments, the working channel 206 and the optical channel 205 have other cross-sectional area shapes and/or configurations. For example, the working channel and the optical channel can be combined into a single channel.

As further illustrated in FIGS. 3A-3D, the access device can act as a conduit for introducing a fluid and/or a distension media into the body through a fluid inlet port 105, and the flow of fluid and/or distension media into the body can be controlled through inflow fluid stopcock 210. The fluid inlet port and/or the inflow fluid stopcock 210 can be positioned perpendicular or substantially perpendicular to the longitudinal axis of the working channel 206. The working channel 206 can be configured to extend the entire length of the access device 104 and comprise a distal exit port 302 that is axially positioned at the distal end of the access device 104. The working channel 206 of the access device 104 can comprise a proximal entry port and/or opening 116 that is axially positioned at the proximal end of the access device 104. The access device 104 can comprise a seal apparatus 304, and a seal cap 306. The seal apparatus 304 is coupled to the access device 104 with the seal cap 306 to prevent fluid from leaking or causing back-spray through the proximal entry port 116. In some embodiments, a surgeon can unscrew the seal cap 306 and replace the seal apparatus with a new seal apparatus configured for a particular instrument to be inserted into the access device 104. The seal apparatus is described below in connection with FIGS. 11-13D.

The access device 104 can comprise an optical system and/or visualization element 204. The optical system 204 within optical channel 205 can comprise an eyepiece 308, a prism (not shown), and a series of rod lenses 207 for visualizing the surgical site, in this case the uterine cavity. In some embodiments, the rod lens 207 has an outer diameter of 2.3 mm; however, in other embodiments, the rod lens 207 can have an outer diameter between 1-3 mm. The optical system 204 can comprise an illumination element for directing light into the surgical area. In some embodiments, a light source is coupled to the light post 310, which is attached to a light delivery medium (for example, a bundle of fiber optics) 312 that traverse the length of the optical channel 205 within the shaft of the access device 104. In some embodiments, the light source can be incorporated into the electrical hardware assembly 110 or into a separate hardware component, wherein the light source is coupled to the light post 310 with fiber optics. In some embodiments, the light source is embedded within the light post 310, which can be removable and/or disposable/reusable. In some embodiments, the light source within the light post 310 is powered by the electrical hardware assembly 110 or some other external power source, or the light source can be powered by a battery system within the light post 310 to reduce the number of cables, tubes, and/or wires connected to the access device, thereby providing the access device increased mobility in some embodiments. The light source can be any of a wide variety of light sources, including but not limited to LED's, halogen lamps, metal halide lamps, xenon arc lamps, or any other light source.

Figure 3:
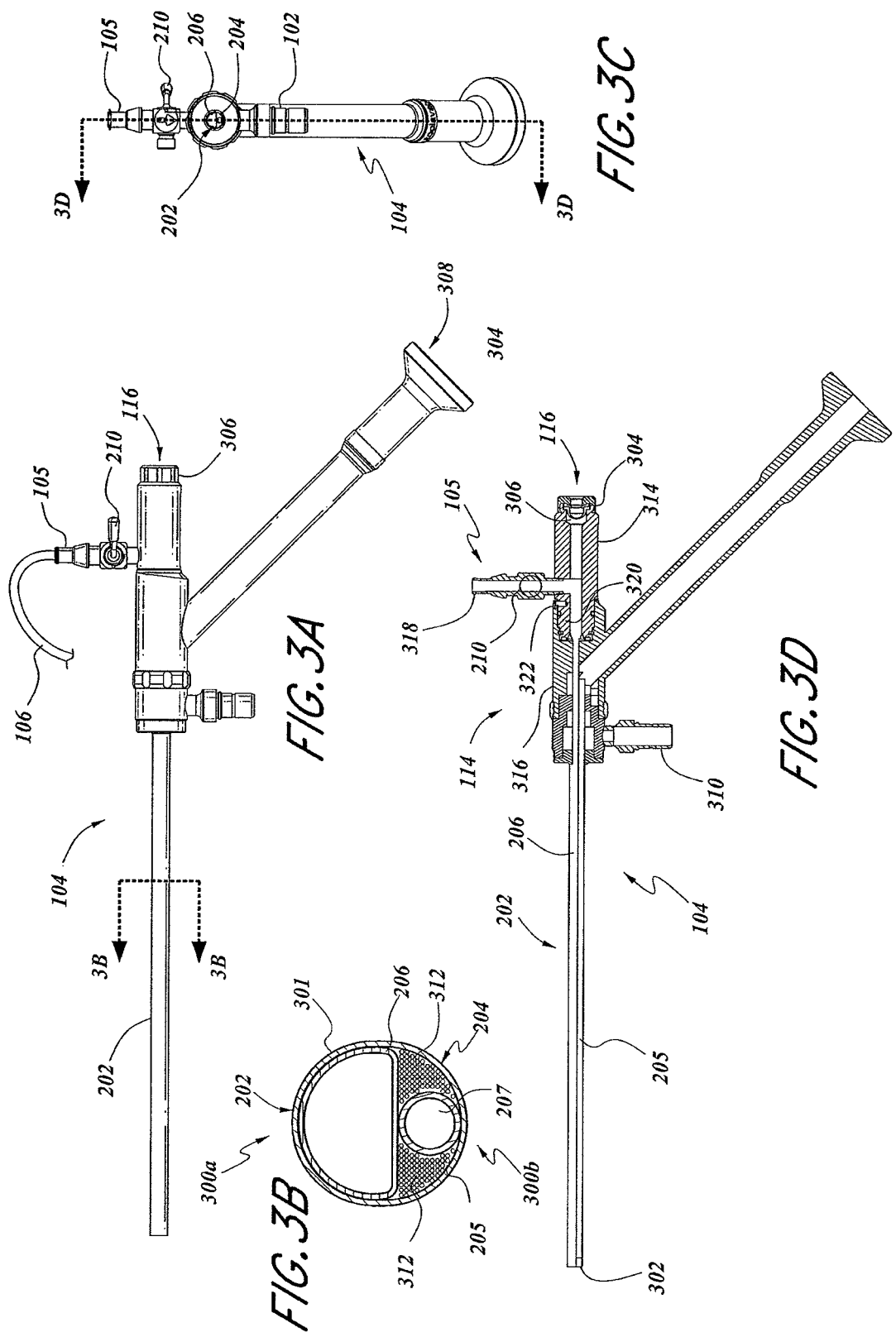
FIG. 3A is a side elevated view of the access device illustrated in FIG. 1.
FIG. 3B is a cross-sectional view of a rod and/or shaft of the access device illustrated in FIG. 1, taken along line 3B-3B.
FIG. 3C is a distal view of the access device illustrated in FIG. 1.
FIG. 3D is a cross-sectional view of the access device illustrated in FIG. 1.
Figure 4:
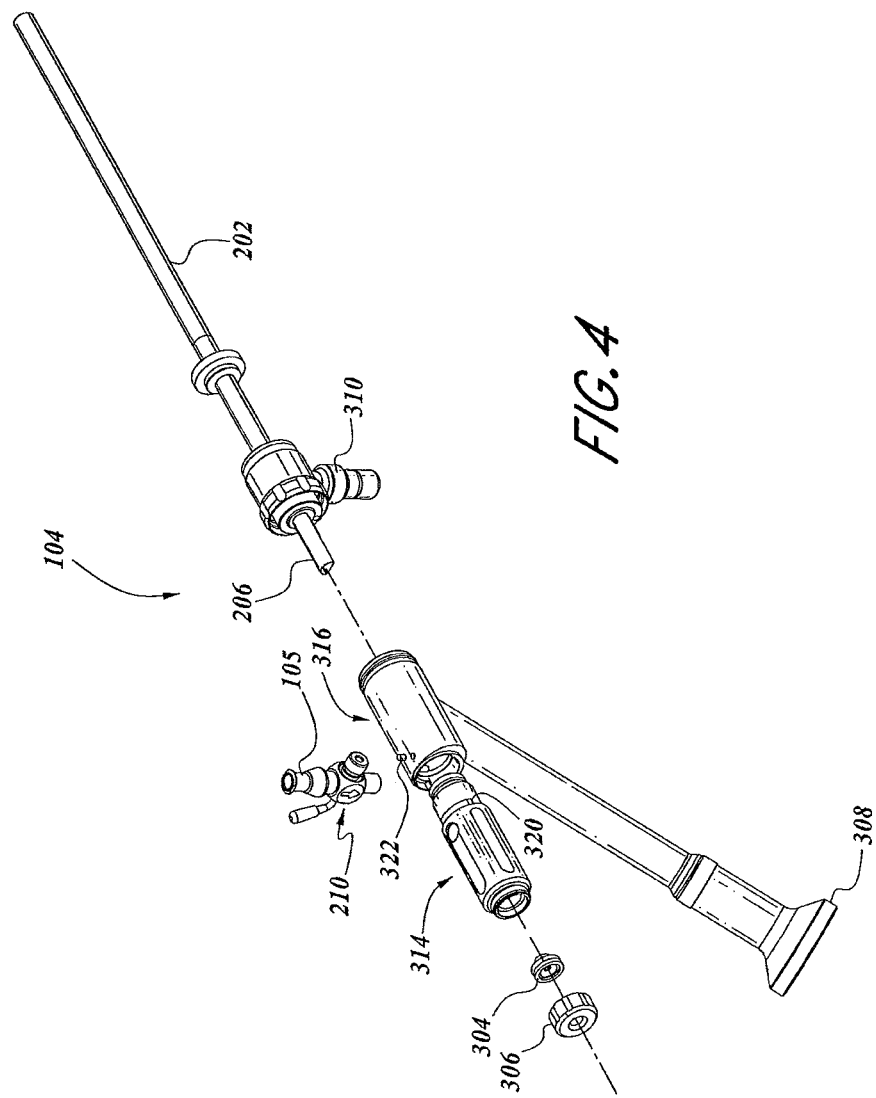
FIG. 4 is a proximal, top, side perspective and exploded view of the access device illustrated in FIG. 1.

With reference to FIGS. 3D-6B, the proximal portion 114 of the access device 104 can comprise an introduction section 314 that is rotatably coupled to an access device body 316 to allow the inflow inlet port 105 to be swiveled and/or rotated 180 degrees about the longitudinal axis of the access device 104. The ability to swivel and/or rotate the inlet portion 105 mitigates the risk of kinking in the inflow tube connecting the fluid supply 106 to the access device 104 through luer fitting 318. In some embodiments, the distal end of the introduction section 314 and the proximal end of the access device body 316 are configured to be coupled and held together with sufficient force by a pin 322 engaging a slot 320 between the introduction section 314 and the access device body 316 while allowing the introduction section 314 to rotate relative to the access device body 316. As illustrated in FIGS. 3D and 4, the access device body 316 comprises the pin 322, the introduction section 314 comprises the rotation slot 320. In some embodiments, the rotation of the introduction section 314 is accomplished by rotating the introduction section 314 relative to the access device body 316, thereby causing the pin 322 to slide along the rotation slot 320. With this configuration, the access device 104 can be configured to be sterilized using high heat or other sterilization means, thereby allowing the access device 104 to be reusable. In other embodiments, the seal between the introduction section 314 and the access device body is accomplished using rubber o-rings and/or other sealing mechanisms, both of which can be configured to be reusable and/or disposable. In some embodiments, the introduction section 314 is a disposable part or portion comprising a rubber o-ring and/or other sealing mechanism configured to form a seal between the introduction section 314 and the reusable access device body 316.

Figure 5:
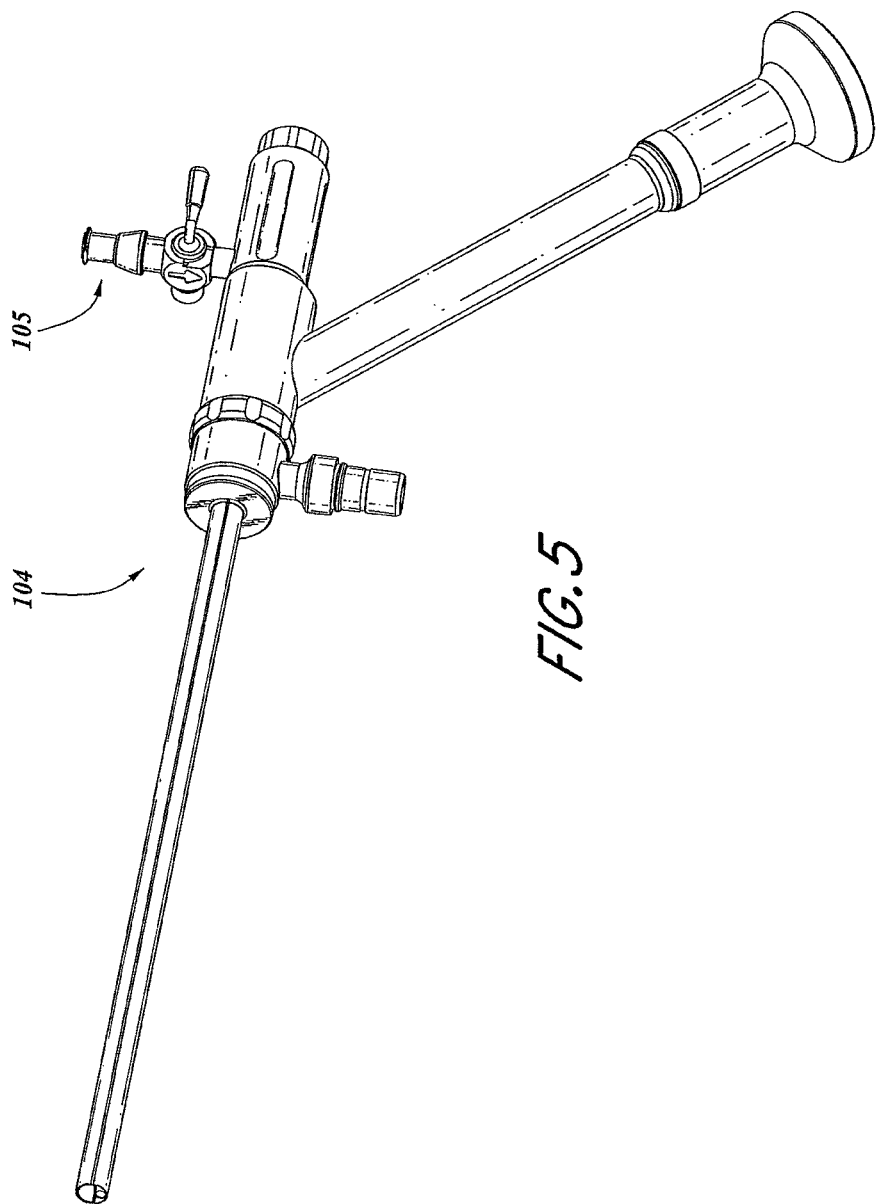
FIG. 5 is bottom, distal, and side perspective view of the access device illustrated in FIG. 1.

As illustrated in FIGS. 5 and 6, the fluid inlet port 105 is positioned in an upward direction (for example, the 12 o'clock position) whereas in FIGS. 6A and 6B, the fluid inlet port 105 is positioned to the side of the access device 104 (for example, the 9 o'clock and 3 o'clock positions). In some embodiments, the fluid inlet port 105 can be rotated 180 degrees between the two side positions; however, in some embodiments, the fluid inlet port 105 can be rotated between the top and bottom positions. In some embodiments, the fluid inlet port 105 can be configured to rotate more than 180 degrees, for example, 360 degrees or substantially 360 degrees. The length of the rotation slot 320, and the positioning of the rotation slot 320 on the introduction section 314 can determine the allowable degree of rotation and/or direction of rotation.

Figure 7:
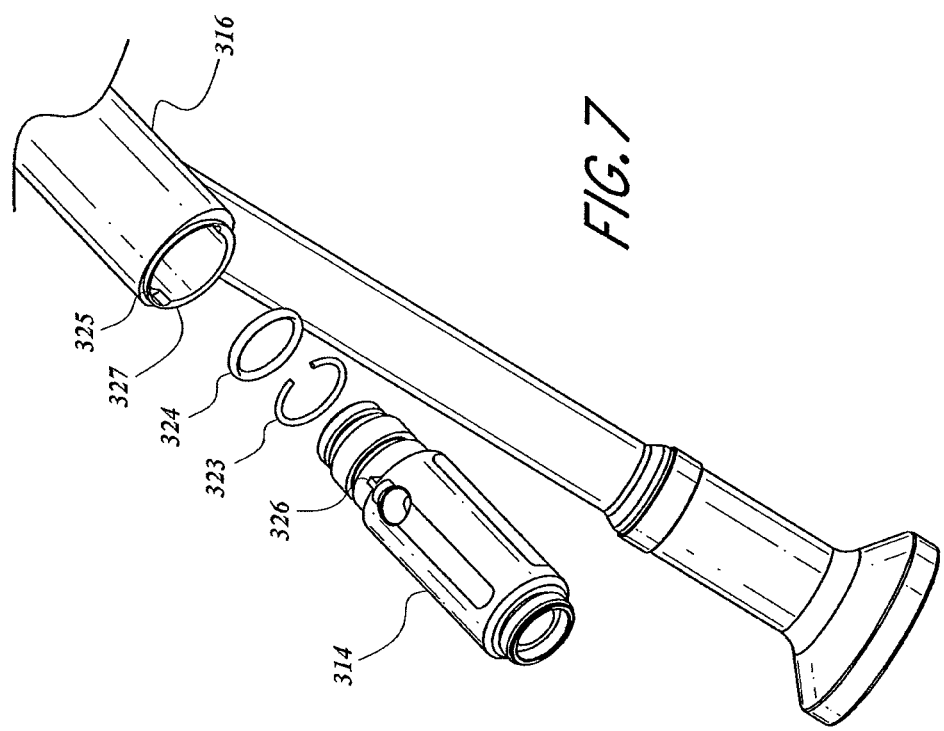
FIG. 7 is a partially exploded perspective of an embodiment of the surgical access device illustrated in FIG. 1.

With reference to FIG. 7, an alternative embodiment for the mounting and rotation of the distal end of the introduction section 314 and the proximal end of the access device body 316 is shown. The mating parts can be configured to be coupled and held together with sufficient force by an internal retention ring 323 engaging a slot 325 between the introduction section 314 and the access device body 316 while allowing the introduction section 314 to rotate relative to the access device body 316. Pin 326 can function as a stop to limit the rotation to 180°. For example, the device body 316 can include a contour 327 with terminal ends disposed 180° apart. The contour 327 can be adapted to receive the pin 326 between the terminal ends and thereby allow the pin 316 and the introduction section 314 rotate between the positions at which the pin 316 contacts the terminal ends of the contour 327. Other configurations can also be used. O-ring 324, or another type of seal, can be used to provide a fluid seal between the mating elements.

Removable Outflow Channel

Figure 8:
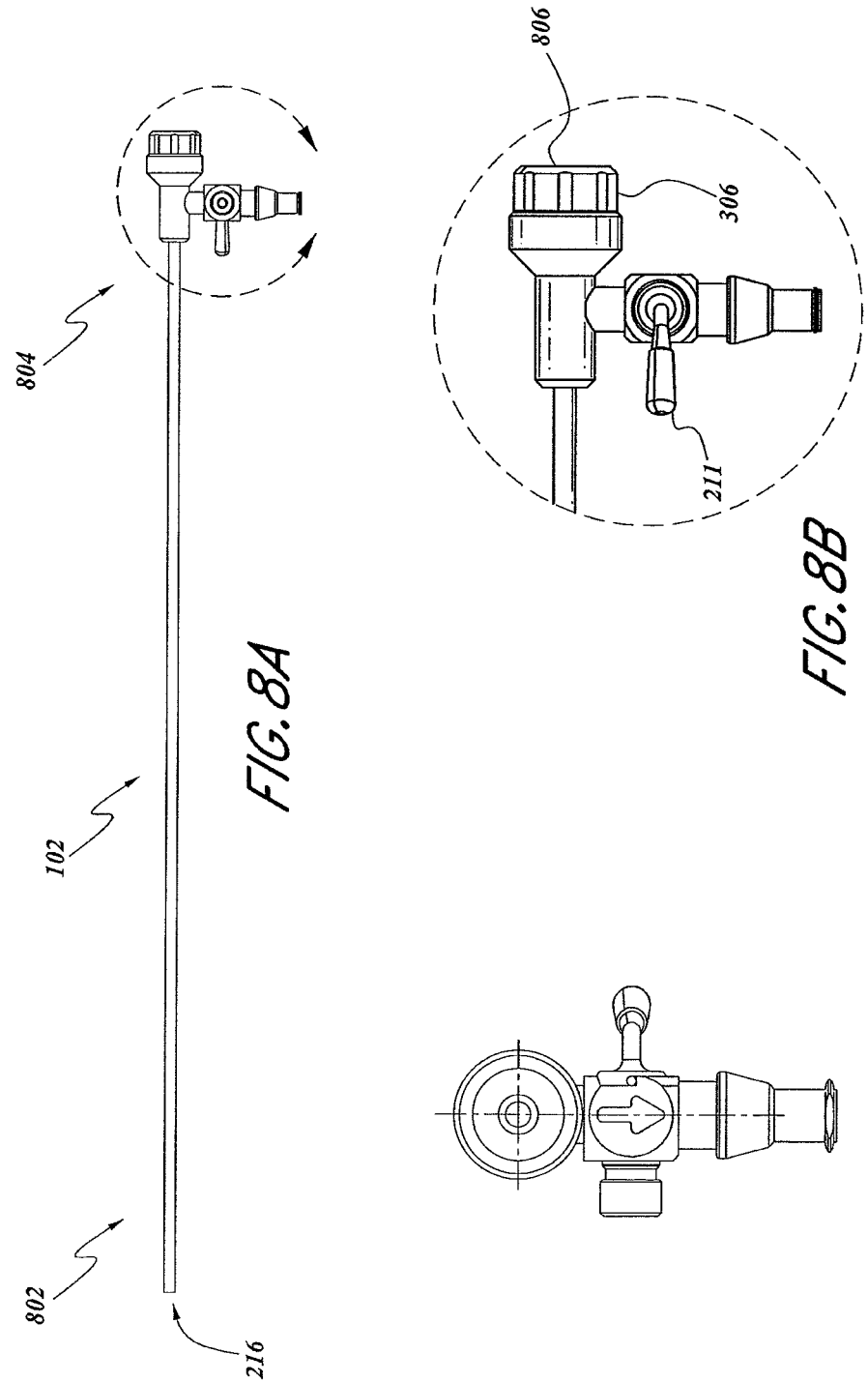
FIG. 8A is a side elevational view of the removable outflow channel illustrated in FIG. 1.
FIG. 8B is a close-up perspective view of the proximal end of the removable outflow channel illustrated in FIG. 1.
FIG. 8C is a proximal elevational view of the removable outflow channel illustrated in FIG. 1.

With reference to FIGS. 8A-8C, there is illustrated an embodiment of the removable outflow channel 102, which can be inserted into the access device 104. The removable outflow channel 102 can comprise can comprise a distal end portion 802 and a proximal end portion 804. The distal end portion 802 can be configured for insertion into the proximal entry port 116 of the access device 104 and through the seal apparatus 304. The distal end portion 802 can be configured to be advanced through the working channel 206 and passed through the distal inflow fluid opening 214 and into the body of the patient. In this case, the removable outflow channel 102 is inserted into a uterine cavity. The removable outflow channel 102 can be inserted through and/or positioned in the working channel 206 while inflow fluid flows in the working channel 206 and around the removable outflow channel 102, and into the body.

The proximal end portion of the removable outflow channel 102 can comprise an outflow fluid stopcock 211, a seal apparatus 304, a seal retainer cap 306, and a proximal entry port 806. The outflow fluid stopcock 211 can be configured to control the flow of outflow fluid from the body. In some embodiments, the seal apparatus 304 and seal cap 306 can be configured to prevent or substantially prevent outflow fluid from back-spraying or leaking out of the proximal entry port 806 of the removable outflow channel 102. In some embodiments, the length of removable outflow channel 102 between the distal outflow fluid opening 216 and the proximal edge of the seal cap 306 has been configured such that the distal outflow fluid opening 216 does not substantially extend beyond the distal inflow opening 214 to form a flush distal tip surface; however, in other embodiments, the length of the removable outflow channel 102 has been configured such that the distal outflow fluid opening 216 extends into the body and beyond the distal inflow opening 214.

Figure 9:
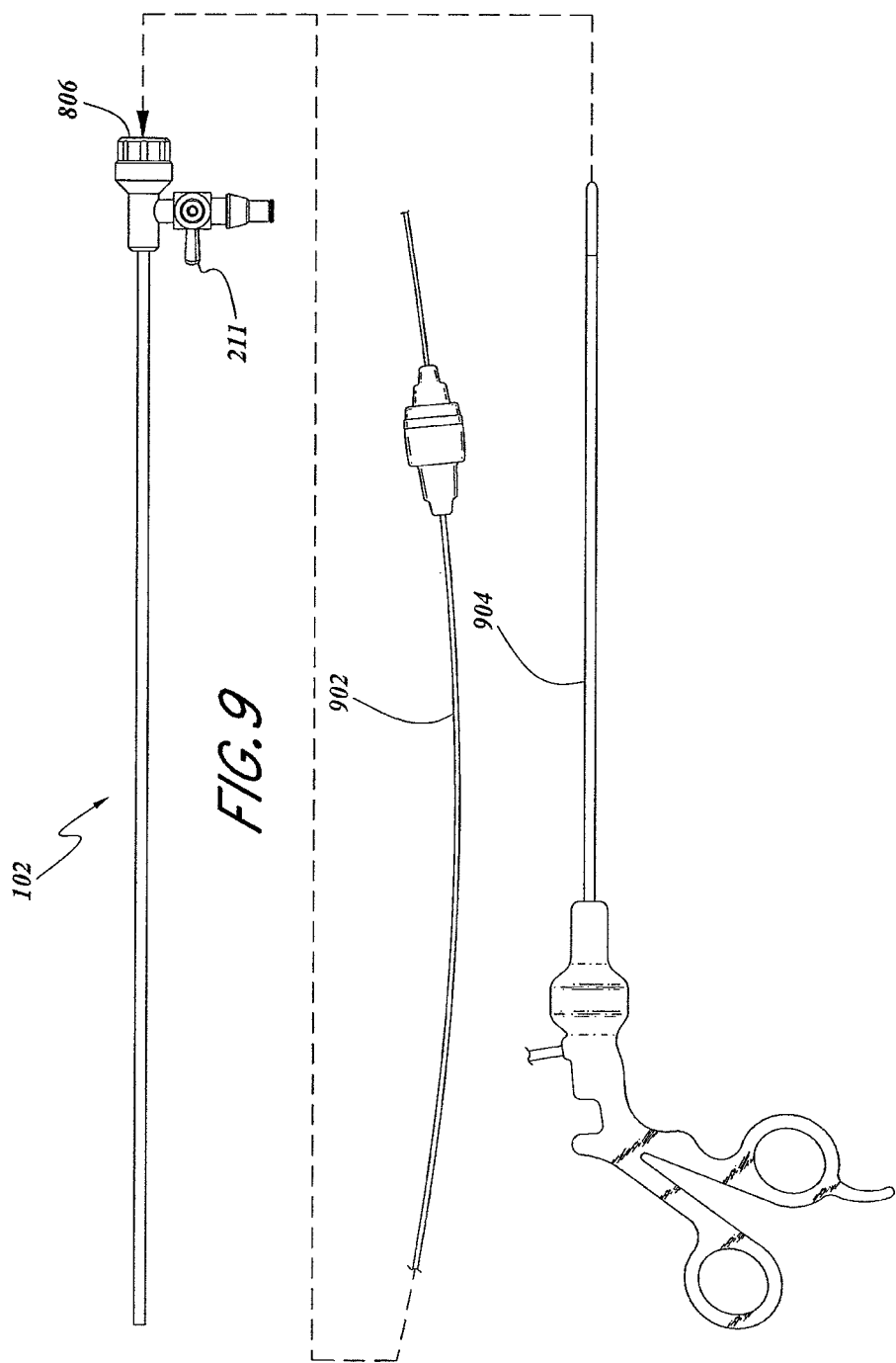
FIG. 9 is a side elevational view of the removable outflow channel illustrated to receive various instruments.

As illustrated in FIG. 9, the proximal entry port 806 of the removable outflow channel 102 can be configured to receive a wide variety of handheld tools and/or instruments for various purposes, for example, diagnosis, biopsy, manipulation, or the like. Examples of the possible handheld tools include without limitation, bx forceps, scissors, dissectors, an electrocautery probe 902, grasper 904, and the like. To accommodate various instruments and/or to provide greater cross-sectional area, the removable outflow channel 102 can comprise various cross-sectional shapes, for example, circular, oval or elliptical, semi-circle-shaped, or any other shape. In some embodiments, the seal apparatus 304 within the removable outflow channel comprises an opening having a shape that conforms or substantially conforms to the shape of the instrument being inserted into the removable outflow channel. In some embodiments, the surgeon can unscrew the seal cap 306 and replace the seal apparatus with a new seal apparatus configured for a particular instrument to be inserted into the removable outflow channel.

Tissue Removal Device

Figure 10:
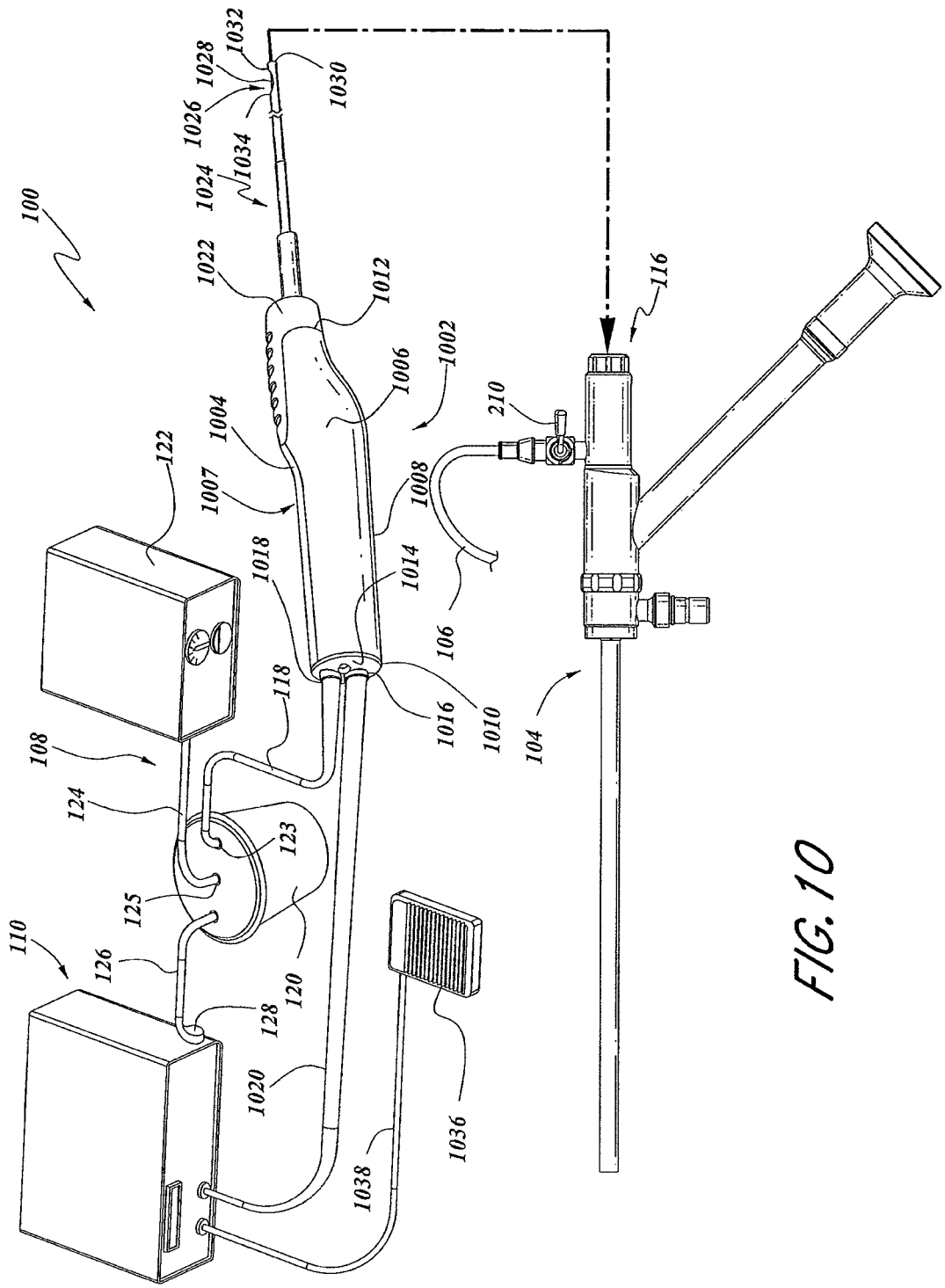
FIG. 10 is a partially exploded perspective of an embodiment of the surgical access system comprising an access device and a tissue removal device.

With reference to FIG. 10, the proximal entry port 116 of the access device 104 can be configured to receive a tissue removal device 1002 for removing tissue from the body, in this case fibroids and other abnormal tissue from the uterine cavity. In some embodiments, the tissue removal device 1002 comprises a lumen or tubular member 1024 for insertion into the working channel 206, in substitution of the removable outflow channel 102, wherein the lumen of the tissue removal device 1002 is connected to a vacuum source 120 for removing outflow fluid, tissue, and/or other matter from the body of the patient.

The tissue removal device 1002 can be of the type described in U.S. patent application Ser. No. 12/432,647, titled "ACCESS DEVICE WITH ENHANCED WORKING CHANNEL," which is hereby incorporated by reference in its entity. The tissue removal device 1002 can comprise complementary left and right housing halves 1004 and 1006, respectively, each of which may be made of a rigid polymer or other suitable material. Halves 1004 and 1006 may be joined together, for example, with screws to form an elongated hollow housing 1007 comprising a rounded side wall 1008, an open proximal end 1010, and an open distal end 1012. Housing 1007 may be bent or otherwise ergonomically shaped to fit comfortably in the hand of a user. A proximal cap 1014 may be mounted in proximal end 1010. The proximal cap 1014 can be configured to comprise a pair of openings or lumens 1016 and 1018. Opening or lumen 1016 can be configured to receive, for example, an external drive shaft, within protective sheath 1020, that is mechanically coupled to a motor within electrical hardware assembly 110. Opening or lumen 1018 can be configured to receive, for example, a outflow tube 118. A distal cap 1022 may be mounted in distal end 1012. The distal cap 1022 can be configured shaped to comprise an opening or lumen, which may be used to receive a shaft or tubular member 1024.

The tubular member 1024 can be configured to be inserted into the working channel 206 of the access device 104 when the removable outflow channel 102 has been removed from the working channel 206. With the tubular member 1024 inserted into the working channel 206, fluid from the fluid supply 106 can enter the body by flowing through inflow fluid stopcock 210 and into the working channel 206 and around the tubular member 1024.

The tubular member 1024 can have an outer diameter of about 3.0 mm for insertion into the working channel 206 of the access device 104. However, in some embodiments, the outer diameter of the tubular member 1024 can be 5.5 mm or less, or more preferably 4 mm or less, even more preferably 3 mm or less, and still even more preferably 2 mm or less. In some embodiments, the tubular member 1024 can comprise a circular cross-sectional shape; however, other cross-sectional shapes (for example, oval or elliptical) are possible to maximize fluid flow and/or tissue cutting and/or removal. With a smaller outer diameter, the tissue removal device 1002 can cause less patient discomfort, reduce the risk of injury to the patient, and/or obviate or reduce the need for anesthesia to be administered to the patient. However, if the tissue removal device 1002 is used in an operating room setting where general anesthesia is available, and/or if the working channel is configured to receive a tissue removal device with a larger diameter, the tubular member 1024 diameter can be increased to maximize tissue removal and/or fluid flow. In such a case, the tubular member 1024 can have a diameter generally less than about 12 mm, preferably less than about 11 mm, and for some applications less than 10 mm. Depending on the particular clinical application, the tubular member 1024 can be constructed to have an outer diameter of no more than about 9 mm, in some applications less than about 8 mm, preferably less than 7 mm, and more preferably less than 6 mm where the outer diameter is desirably minimized.

In some embodiments, the tubular member 1024 can comprise an opening or resection window 1026 with a cutting mechanism 1028 moving rotationally and, at the same time, oscillating translationally relative to tubular member 1024. In some embodiments, the tubular member 1024 is connected to the outflow tube 118 through lumen 1018.

When a vacuum is applied to tubular member 1024, the resection window 1026 can be configured to receive, capture, and/or draw in tissue, fluid, and/or other matter. In some embodiments, the window 1026 can be located proximate to the distal end 1030 of the tubular member, such as, for example, 3 mm from distal end 1030. The resection window 1026 can be shaped to comprise a distal end 1032 and a proximal end 1034. The proximal end 1034 can slope gradually proximally, and the distal end 1032 can slope gradually distally. In some embodiments, the slopes of the proximal and distal ends 1032, 1034 allow or encourage tissue to enter the resection window. In some embodiments, the slopes of the proximal and distal ends 1032, 1034 form cutting edges for tissue resection. In some embodiments, the resection window 1026 can have a length of approximately 0.55 inches; however, other lengths are possible. The proximal end 1034 of the resection window 1016 can be a radial end having a radius of curvature of, for example, 0.085 inches; however, other radius curvatures are possible. The distal end 1032 of resection window 1016 may be a radial end having a radius of curvature of, for example, 0.150 inches; however, other radius curvatures are possible. In some embodiments, the resection window 1026 can extend over a substantial portion of the circumference of tubular member 1024, such as, for example, about 60% of the circumference; however, other percentages are possible.

The vacuum assembly 108 can comprise a specimen collection/fluid container 120 and a vacuum source 122. The distal end of a outflow tube 118 can be connected to the proximal end of vacuum tube 124, and the proximal end of outflow tube 118 can be coupled to a first port 123 of container 120. The distal end of a tube 124 can be coupled to a second port 125 of container 120, and the proximal end of tube 124 can be coupled to the vacuum source 122. In this manner, the vacuum source 122 can be used to apply suction to the tissue removal device 1002, and any withdrawn tissue, fluids, or other matter suctioned through the resection window 1026 of the tissue removal device 1002 may be collected in container 120.

The motor connected to the drive shaft within protective sheath 1020 can be coupled to a source of electricity, such as an AC wall outlet, using a power cord (not shown), and/or can be included within electrical hardware assemble 110, in which there may be disposed other electronics (not shown). A foot pedal 1036 can be coupled to the motor by a cable 1038, and the foot pedal 1036 can be used as a power switch to selectively activate or de-activate the motor. The proximal end of drive shaft can be mechanically coupled for rotation to the motor, and the distal end of drive shaft can be inserted through opening 1016 in the proximal cap 1014, and coupled to the tissue removal device 1002 for tissue resection.

The electrical hardware assembly 110 can include a vacuum sensor 128, which can be coupled to the container 120 by a tube 126, so that the pressure within the container 120 may be monitored. In this manner, a sudden increase in vacuum pressure can indicate that a clog has occurred. The presence of a clog can be indicated via an alarm (not shown) located on or within the electrical hardware assembly 110.

The detection of a clog can indicate that further operation of the tissue removal device 1002 can only aggravate the clogging situation and that a cessation of tissue removal may be necessary. In this case, the electrical hardware assembly 110 can be configured to turn off and/or deactivate the vacuum source 122 and/or the motor. Similarly, a decrease in vacuum pressure, sudden or otherwise, can indicate that the tissue removal device 1002 and/or the removable outflow channel has been removed from the working channel 206 of the access device 104. With the tissue removal device 1002 and/or the removable outflow channel removed, the inflow fluid cannot be removed from the body. In this case, the electrical hardware assembly 110 can be configured to turn off and/or deactivate the fluid supply 106 and/or the vacuum device.

The electrical hardware assembly 110 can be configured to synchronize actuation of the motor with actuation of vacuum source 122. In this manner, turning on the motor will turn on the vacuum source 122 at the same time. Correspondingly, vacuum source 122 may be deactivated whenever the motor is turned off or when the tissue removal device 1002 and/or the removable outflow channel 102 is removed from the access device 104.

Seal Apparatus

With reference to FIGS. 11-12H, the access device 104 and the removable outflow channel 102 can both comprise a seal apparatus 304 as described above. The seal apparatus 304 can be configured to maintain intra-cavity pressure of the body (in this case, the uterine cavity) and/or the prevention of back-spray toward the surgeon, thereby protecting the surgeon from blood borne pathogens in the back-spray. The seal apparatus 304 can prevent or substantially prevent leakage of fluids (for example, distension media, blood, and other matter) in at least four different modes: 1) when no instrument 1204 is inserted through the seal apparatus of the access device 104; 2) when the removable outflow channel 102 is inserted through the seal apparatus of the access device 104, for example, for diagnostic uses; 3) when no instrument 1204 is inserted through the seal apparatus of the removable outflow channel 102; and 4) when the tissue removal device is inserted through the seal apparatus of the access device 140, for example, for therapeutic uses. In some embodiments, the seal apparatus within the removable outflow channel 102 and the access device 104 can be substantially the same; however, in some embodiments, the seal apparatus can differ in design, shape, configuration, and dimensions.

In this case where the seal apparatuses are substantially the same, both the removable outflow channel 102 and the access device 104 comprise a threaded connection 1110 located at the proximal end of the removable outflow channel 102 and the access device 104. The seal apparatus 304 can be positioned within the lumen 1112 of the threaded connection 1110 and/or the rim, edge, or platform 1120 of seal apparatus 304 can be configured to rest against rim or edge or platform 1114. In some embodiments, the seal apparatus 304 comprises a thickness such that a portion of the seal apparatus 304 protrudes from the lumen 1112. When the seal cap 306 is screwed onto the threaded connection 1110, the seal cap can be configured to compress the seal apparatus 304 thereby securing the seal apparatus and forming a seal between the threaded connection 1110 and the seal cap 306. In some embodiments, the seal apparatus 304 comprises a thickness that allows the seal apparatus 304 to be flush against the proximal end 1116 of the threaded connection 1110. In this embodiment, the seal cap 306 can comprise a protrusion portion 1118 configured to press against the seal apparatus 304 when the seal cap 306 is screwed onto the threaded connection 1110, thereby securing the seal apparatus and forming a seal between the threaded connection 1110 and the seal cap 306.

In some embodiments, the seal apparatus 304 comprises a circular seal portion 1102 having an opening 1104, and a dome-shaped or hemispherical seal portion 1106. The circular seal portion 1102 can be configured to seal around the outer perimeter of a shaft of an instrument 1204 inserted through the opening 1104 of the circular seal portion 1102. In some embodiments, the opening 1104 is circular and/or round in shape to form a seal around a shaft having a round cross-sectional area; however, a wide variety of shapes for opening 1104 are possible to correspond to the instruments 1204 being inserted through the circular seal portion 1102. For example, the opening 1104 can comprise a substantially oval-shaped configuration if the to be inserted instrument 1204 had a shaft having an oval cross-sectional shape.

The dome-shaped or hemispherical seal portion 1106 can comprise a slit 1108 within the dome portion of the hemispherical seal portion 1106. In some embodiments, the dome-shaped seal 1106 can be configured to allow an instrument 1204 to pass through the slit 1108. As the instrument passes through the slit 1108, the dome portion splits apart to form bent portions 1206 that slide along the outer perimeter of the instrument 1204. When the insertion of an instrument causes the dome portion to split apart, gap areas 1208 can be created to allow fluid into the seal apparatus 304. Fluid is prevented or substantially prevented from exiting the seal apparatus 304 because the circular seal portion 1102 forms a seal with the outer perimeter of the instrument 1204.

In some embodiments, the dome-shaped seal portion 1106 can be configured to seal the fluid within the working channel 206 when no instrument 1204 has been inserted through slit 1108. The dome-shaped seal portion 1106 comprises more than one slit, for example, two, three, four, five, six, seven, eight, or more slits. In some embodiments, the plurality of slits is configured in a star pattern; however, a wide variety of patterns are possible.

In some embodiments, the slit or plurality of slits 1108 is formed using a cutting edge that cuts through the dome portion from the concave side to create a bias in the slit, wherein the bias allows the slit to form a seal or a substantially tight seal when there is fluid pressure (from the working channel 206) on the convex side of the dome seal. In some embodiments, the slit 1108 can be formed with a cutting edge that cuts the dome portion from the convex side. In some embodiments, the cutting edge is a razor or knife or other cutter that cuts in a radial fashion that corresponds to the curvature of the dome. In some embodiments, a surface is placed on the convex side of the dome portion while the cutting edge cuts the dome-shaped seal 1106 from the concave side so as to prevent the dome portion from substantially stretching while the cutting edge forms the slit 1108. In some embodiments, the cutting edge uses laser technology, microwave technology, ultrasound technology, and/or other technology to form the slit 1108 within the dome-shaped seal 1106. In some embodiments, the length of the slit can be 1 mm, 2 mm, 3 mm, 4 mm, 5 mm, 6 mm, or any other suitable length to allow a desired instrument 1204 to pass through the seal apparatus 304.

The seal apparatus 304 can be manufactured from a variety of elastic materials with high elongation capacity, for example, silicone, EDPM rubber, polyurethane or fluoroelastomers (Viton®), or the like. In some embodiments, the circular seal portion 1102 and the dome-shaped seal portion 1106 are manufactured from the same material having the same elasticity and/or elongation capacity; however, in some embodiments, the circular seal portion 1102 and the dome-shaped seal portion 1106 can be manufactured from different materials having different elasticity and/or elongation capacity. In some embodiments, the dome-shaped seal portion 1106 is manufactured from a material having a more durable characteristic to allow the dome portion to withstand the fluid pressure from the working channel 206 and to form a seal. In some embodiments, the circular seal portion 1102 is manufactured from a material having a highly elastic characteristics and/or elongation capacity to allow instruments 1204 to pass through the opening 1104 and to form a seal around the outer surface of the inserted instrument 1204. In some embodiments, the circular seal portion 1102 and/or the dome-shaped seal portion comprise reinforcement material in all or parts of the circular seal portion 1102 and/or the dome-shaped seal portion. The reinforcement material can comprise without limitation metals, polymers, or other suitable materials, and/or the reinforcement material can take the form of filaments, scaffolding, meshes, membranes, or the like, In some embodiments, the circular seal portion 1102 and the dome-shaped seal portion 1106 can have uniform thickness; however, in some embodiments, different parts of the circular seal portion 1102 and/or the dome-shaped seal portion 1106 have different thicknesses. For example, the circular seal portion 1102 can comprise a seal face section 1202 having a thickness of about 0.010 to 0.020 inches thick to permit the material to elongate without tearing when an instrument 1204 passes through the opening 1104. In some embodiments, the circular seal portion 1102 can comprise a flat section 1210 having a thickness of about 0.020 to 0.040 inches thick to allow for durability when compressed by the seal cap 306 and/or when integrated with and/or bonded with the dome-shaped seal portion 1106. In some embodiments, the dome-shaped seal portion 1106 can comprise a thickness of about 0.010 to 0.020 inches thick to permit the material to elongate and slide open without tearing when an instrument 1204 passes through the slit 1108. In some embodiments, the dome-shaped seal portion 1106 can comprise thicker regions in the base of the dome portion, while the areas closest to the slit are thinner. Thicker regions in the base provide for more stability for the dome portion while thinner regions around the slit area provide for more elasticity and/or elongation, allowing for easier passage of an instrument through the slit. In some embodiments, the dome-shaped seal portion 1106 can comprise a flat area 1212 to be integrated with and/or bonded with the circular seal portion 1102. The dome-shaped seal portion 1106 and the circular seal portion 1102 can be integrated and/or bonded together in a variety of ways, for example, adhesion, fusion, melting, or any other process.

Figure 13C:
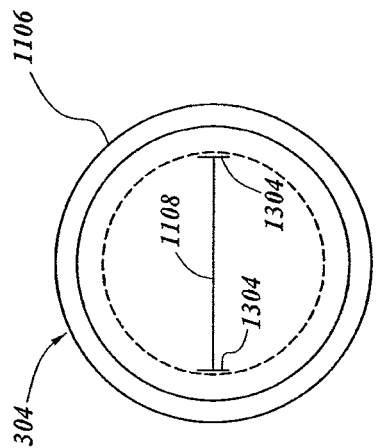
FIGS. 13A-13C are distal views of various embodiments of the seal apparatus.
Figure 13B:
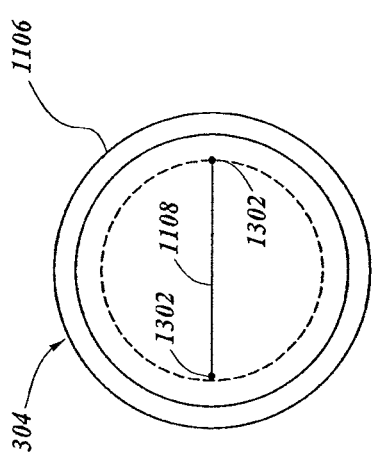
Figure 13D:
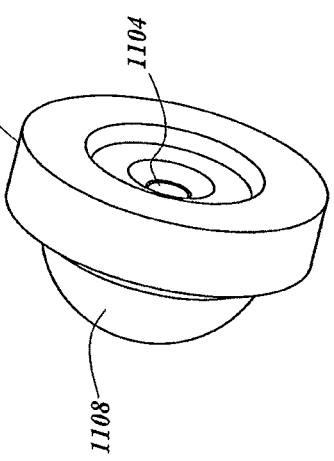
FIG. 13D is a proximal, bottom, and side perspective view of an embodiment of the seal apparatus.
Figure 13A:
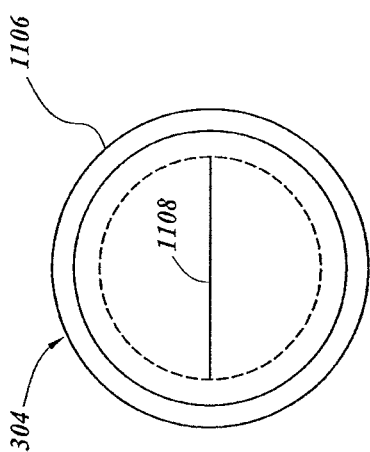

With reference to FIGS. 13A-13C, there is illustrated a distal view of various embodiments of the seal apparatus 304. As illustrated in FIGS. 13B-13C, the slit 1108 can comprise stress relief areas to prevent the slit 1108 from tearing as an instrument 1204 passes through the slit 1108. In some embodiments, the stress relief area 1302 in FIG. 13B comprises a circular cut region to substantially prevent the slit 1108 from tearing. In some embodiments, the stress relief area 1304 in FIG. 13C comprises a transverse cut region to substantially prevent the slit 1108 from tearing. In some embodiments, the stress relief area can comprise other types of cut regions and/or can comprise thicker material and/or can comprise reinforcement materials to prevent tearing of the slit 1108.

With reference to FIG. 13D, there is illustrated an embodiment of the seal apparatus 304 as single monolithic part as opposed to an integrated part formed by a circular seal portion 1102 and a dome-shaped seal portion 1106. In some embodiments, the single monolithic part is formed by an injection mold process using silicone, EDPM rubber, polyurethane or fluoroelastomers (Viton®), or the like. In some embodiments, a single material is used to construct the monolithic part, and in other instances, two or more materials in used during the injection mold process to allow different portions of the monolithic part to comprise areas having different elasticity, elongation, durability, and the like. With the single monolithic part, a protector or trocar can be inserted into the opening 1104 to prevent the opening 1104 from being cut by the cutting edge used to form the slit 1108 on the concave surface of the dome portion of the seal apparatus 304.

Figure 14A:
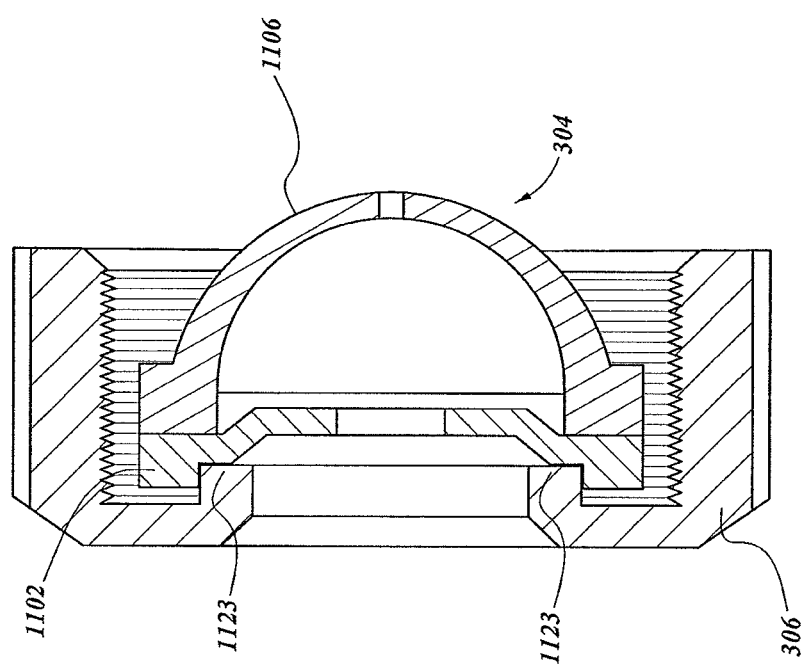
FIG. 14A is side perspective view of an embodiments of the seal apparatus for the access device.
Figure 14B:
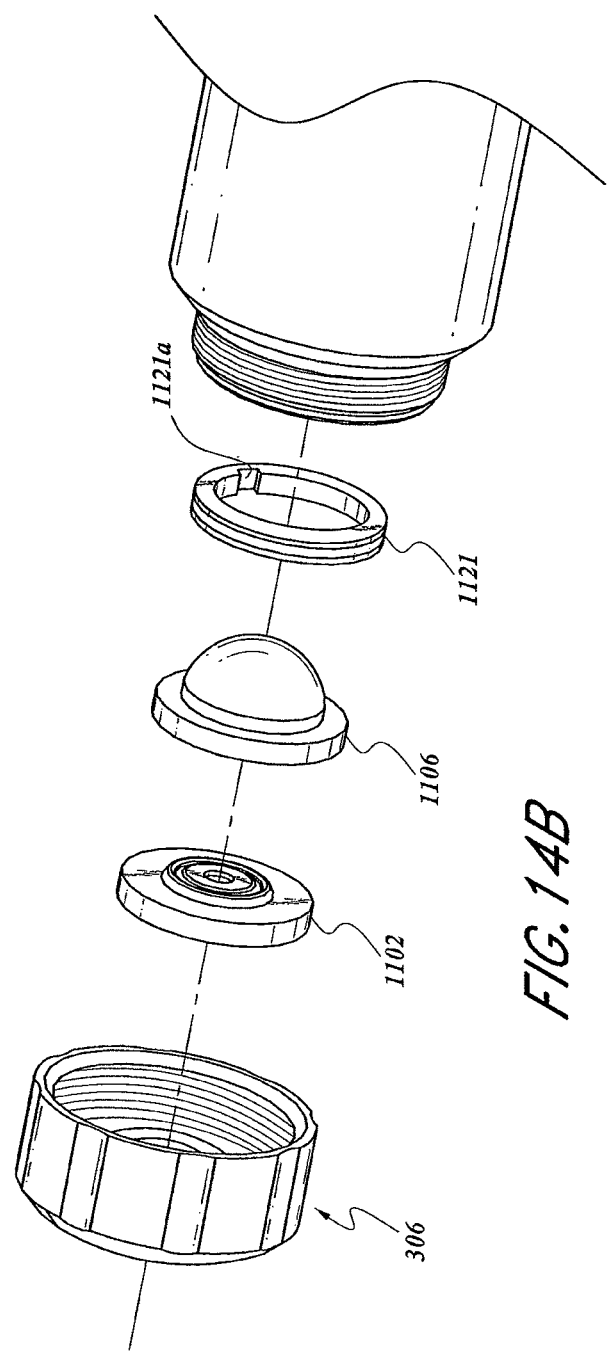

With reference to FIGS. 14A-14C, further embodiments of the seal apparatus 304 and seal cap 306 are illustrated. FIG. 14A illustrates the use of an adhesive 1123 to bond the seal apparatus 304 to the seal cap 306. Bonding as such can provide further advantages, such as but without limitation, the entire assembly can now be offered as a single use component eliminating or reducing the need for handling the seal apparatus 304 prior to use. The seal cap 306 can be made from a low cost plastic material, stainless steel, or other materials. The seal apparatus 304 can be bonded with an inexpensive adhesive such as a cyanoacrylate, epoxy, silicone, or other adhesives.

FIG. 14B illustrates another modification of the seal apparatus 304, in which a mechanical locking ring 1121 can be threaded into the seal cap 306 to lock the seal apparatus 304 in place. With this configuration, the mating surface 1114 in the hysteroscope 104 or outflow channel 102 can be eliminated and the two seals 1102, 1106 can be sufficiently compressed into a sealing engagement without an adhesive.

In some embodiments, the locking ring 1121 can optionally include an engagement portion 1121a configured to allow a tool to be engaged with the locking ring 1121 and thus make assembly more convenient. In some embodiments, the engagement portion 1121a can be in the form of a keyway or similar recess. A tool having a face complementary to an axial facing surface of the locking ring 1121 and the keyway can be used to tighten the locking ring 1121. However, other configurations and tools can also be used.

In another modification of the seal apparatus 304, illustrated in FIG. 14C, which can be in the form of a single use seal apparatus, an internal retaining ring 1122 can be "snapped" into the seal cap 306 to lock the seal apparatus in place. For example, the internal retaining ring 1122 can be in the form of a split ring configured with a sufficient outward bias to secure itself within the seal 306. With this configuration, the mating surface 1114 in the hysteroscope 104 or outflow channel 102 can be eliminated and the seals 1102, 1106 can also be sufficiently compressed into a sealing engagement without an adhesive.

FIGS. 15A-15E illustrate removable and/or disposable sheaths for inserting into the working channel 206 of the access device 104. In FIG. 15A, there is illustrated a sheath 1402 inserted within the working channel 206 of the access device 104 to prevent or substantially fluid, blood, and/or other materials from contacting the inner surface of the working channel 206, thereby allowing the working channel 206 to require little to no sterilization after use. In some embodiments, the inner channel of the removable and/or disposable sheath is divided into one or more channels as illustrated in FIGS. 15C-15E. In some embodiments, the one or more channels are formed by a wall. In some embodiments, the sheaths can be configured be inserted into the working channel as well as around the outer surface of the access device 104 to prevent or substantially prevent the outer and/or inner surfaces of the access device 104 from contacting the body, fluids, and/or materials. The removable and/or disposable sheath can be manufactured from a wide variety of materials, including without limitation silicone, EDPM rubber, polyurethane or fluoroelastomers (Viton®), or the like.

Method of Use

The surgical access and removable system 100 can be used in a variety of different ways and in a variety of contexts. In some embodiments, a method for use comprises insertion of the access device within an orifice of the body or an incision in the body. In this case, the hysteroscope is inserted through the cervix and into the uterine cavity. The access device is connected to a fluid supply to introduce a distension media into the body. In this case, the distension media distends the uterine cavity to improve visualization the flaccid organ. In some embodiments, the fluid supply is configured to detect pressure within the body (for example, the uterine cavity) and to maintain a specific pressure.

To perform diagnostic procedures, the removable outflow channel is inserted through the proximal entry port of the access device. As the removable outflow channel is inserted through the seal apparatus, the removable outflow channel moves into a first position where the outer perimeter of the removable outflow channel forms a seal with the circular seal portion. As the removable outflow channel is advanced further into the seal apparatus, the removable outflow channel moves into a second position where the removable outflow channel passes through the slit of the dome portion of the seal apparatus and into the working channel of the access device. In moving the removable outflow channel into working channel, a fluid pathway is opened between the working channel and the seal apparatus; however, fluid is prevented from leaking out of the seal apparatus because of the seal made between the circular seal portion and the removable outflow channel. The removable flow channel is advanced to the distal end of the access device. The removable outflow channel is connected to a vacuum source, and fluid within the body starts to flow through the removable outflow channel while inflow fluid flows within the working channel and around the removable outflow channel and into the body. A light source is connected to the light post on the access device to deliver light into the body. The surgeon can visualize the uterine cavity through the eyepiece on the access device.

The surgeon can insert various instruments into the removable outflow channel. Insertion of instruments can be completed by inserting the instrument through the proximal entry port of the removable outflow channel. The proximal entry port also has a seal apparatus. As the instrument is inserted through the seal apparatus, the instrument moves into a first position where the outer perimeter of the instrument forms a seal with the circular seal portion. As the instrument is advanced further into the seal apparatus, the instrument moves into a second position where the instrument passes through the slit of the dome portion of the seal apparatus and into the removable outflow channel. In moving the instrument into the lumen of the removable outflow channel, a fluid pathway is opened between the removable outflow channel and the seal apparatus; however, fluid is prevented from leaking out of the seal apparatus because of the seal made between the circular seal portion and the instrument. The instrument is advanced to the distal end of the removable outflow channel and into the body.

The instrument may be retracted from the body. In retracting the instrument through the seal apparatus of the removable outflow channel, the instrument enters a first position where the instrument passes out of the dome-shaped seal portion to allow the dome-shaped seal portion to form a seal to close the fluid pathway between the removable outflow channel and the seal apparatus. As the instrument is further retracted, the instrument enters a second position where the instrument passes out of the circular seal portion. There is little or no back-splash because the fluid path between the removable outflow channel and the seal apparatus has been closed by the dome-shaped seal portion.

The removable outflow channel may also be retracted from the body and/or the access device. In retracting the removable outflow channel through the seal apparatus of the access device, the removable outflow channel enters a first position where the removable outflow channel passes out of the dome-shaped seal portion to allow the dome-shaped seal portion to form a seal to close the fluid pathway between the working channel and the seal apparatus. As the removable outflow channel is further retracted, the removable outflow channel enters a second position where the removable outflow channel passes out of the circular seal portion. There is little or no back-splash because the fluid path between the access device and the seal apparatus has been closed by the dome-shaped seal portion. In some embodiments, the fluid supply is configured to stop pumping fluid into the body when the removable outflow channel has been removed from the working channel because there is no mechanism for removing fluid from the body.

To remove tissue from the body, in this case the uterine body, the surgeon can insert a tissue removal device into the access device. As the tissue removal device is inserted through the proximal entry port of the access device, the tissue removal device enters the seal apparatus of the access device. In advancing the tissue removal device through the seal apparatus, the tissue removal device enters into a first position where the outer perimeter of the tissue removal device forms a seal with the circular seal portion. As the tissue removal device is advanced further into the seal apparatus, the tissue removal device moves into a second position where the tissue removal device passes through the slit of the dome portion of the seal apparatus and into the working channel of the access device. In moving the tissue removal device into working channel, a fluid pathway is opened between the working channel and the seal apparatus; however, fluid is prevented from leaking out of the seal apparatus because of the seal made between the circular seal portion and the tissue removal device. The tissue removal device is advanced to the distal end of the access device and into the body. The tissue removal device is connected to a vacuum source, and fluid within the body starts to flow through the tissue removal device while inflow fluid flows within the working channel and around the tissue removal device and into the body. The tissue removal device is connected to a drive shaft, which is drive by a motor. By activating the motor, the drive shaft drives the cutting device within the tissue removal device to cut tissue within the body, in this case the uterine cavity. By visualizing the target tissue through the eye, the surgeon can use the tissue removal device to perform tissue resection.

The tissue removal device may be retracted from the body. In retracting the tissue removal device through the seal apparatus of the access device, the tissue removal device enters a first position where the instrument passes out of the dome-shaped seal portion to allow the dome-shaped seal portion to form a seal to close the fluid pathway between the working channel and the seal apparatus. As the tissue removal device is further retracted, the tissue removal device enters a second position where the tissue removal device passes out of the circular seal portion. There is little or no back-splash because the fluid path between the working channel and the seal apparatus has been closed by the dome-shaped seal portion.

Conditional language, such as, among others, "can," "could," "might," or "may," unless specifically stated otherwise, or otherwise understood within the context as used, is generally intended to convey that some embodiments include, while other embodiments do not include, some features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Although this invention has been disclosed in the context of some preferred embodiments and examples, it will be understood by those skilled in the art that the present invention extends beyond the specifically disclosed embodiments to other alternative embodiments and/or uses of the invention and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. Thus, it is intended that the scope of the present invention herein disclosed should not be limited by the particular disclosed embodiments described above.

Although the embodiments of the inventions have been disclosed in the context of a some preferred embodiments and examples, it will be understood by those skilled in the art that the present inventions extend beyond the specifically disclosed embodiments to other alternative embodiments and/or uses of the inventions and obvious modifications and equivalents thereof. In addition, while a number of variations of the inventions have been shown and described in detail, other modifications, which are within the scope of the inventions, will be readily apparent to those of skill in the art based upon this disclosure. It is also contemplated that various combinations or subcombinations of the specific features and aspects of the embodiments may be made and still fall within one or more of the inventions. Accordingly, it should be understood that various features and aspects of the disclosed embodiments can be combine with or substituted for one another in order to form varying modes of the disclosed inventions. For all of the embodiments described herein the steps of the methods need not be performed sequentially. Thus, it is intended that the scope of the present inventions herein disclosed should not be limited by the particular disclosed embodiments described above.

What is claimed is:

1. A method of accessing an internal site in a patient's uterus, comprising:
    positioning a hysteroscope into an inserted position by inserting a distal end of the hysteroscope, from an outside of a body of a patient, through a cervix of the patient, into a position within the patient's uterus, the hysteroscope comprising a proximal end and an elongate body extending from the proximal end to the distal end, the elongate body having a working channel extending axially therethrough;
    fluidly connecting the working channel to an inflow fluid source for introducing inflow fluid into the patient's uterus through the working channel;
    inserting axially a removable outflow channel through the working channel, the removable outflow channel having a lumen extending between a distal end and a proximal end of the removable outflow channel, wherein the distal end of the removable outflow channel does not substantially extend beyond the distal end of the hysteroscope;

fluidly connecting the removable outflow channel to a vacuum source for removing inflow fluid from the patient's uterus through the removable outflow channel;

distending the patient's uterus by introducing inflow fluid into the working channel and into the uterus;

removing the removable outflow channel from the working channel, while maintaining the hysteroscope in the inserted position such that the distal end of the hysteroscope remains within the patient's uterus, by proximally retracting the removable outflow channel to a first position to thereby close a seal device coupled to the proximal end of the hysteroscope, wherein the seal device prevents inflow fluid from exiting out of the proximal end of the hysteroscope;

after removing the removable outflow channel from the working channel, advancing axially a surgical instrument through the working channel and into the patient's uterus, the surgical instrument comprising a tissue morcellator having an internal outflow channel; and fluidly connecting the internal outflow channel of the morcellator to a vacuum source for removing inflow fluid from the patient's uterus through the internal outflow channel.

2. The method of claim 1, wherein inserting axially the removable outflow channel through the working channel further comprises opening the seal device and generating a seal between an outer surface of the removable outflow channel and the hysteroscope.

3. The method of claim 1, wherein the seal device comprises a first sealing element and a second sealing element, the first sealing element positioned distal relative to the second sealing element.

4. The method of claim 3, wherein retracting the removable outflow channel to the first position closes the first sealing element to prevent inflow fluid from exiting out of the proximal end of the hysteroscope, while the second sealing element maintains a seal around the removable outflow channel to prevent back splash as the first sealing element closes.

5. The method of claim 1, further comprising advancing axially a surgical tool through the removable outflow channel and into the patient's uterus.

6. The method of claim 1, wherein fluidly connecting the working channel to an inflow fluid source creates an inflow fluid path.

7. The method of claim 6, wherein closing the seal device closes the inflow fluid path.

8. The method of claim 6, wherein the seal device comprises a first sealing element and a second sealing element, the first sealing element positioned distal relative to the second sealing element, wherein the removing the removable outflow channel to the first position closes the inflow fluid path, and wherein further proximally retracting the removable outflow channel to a second position closes the second sealing element.

9. The method of claim 8, wherein at least one of the first or second sealing elements comprises a dome-shaped portion having at least one slit opening.

10. The method of claim 9, wherein the dome-shaped portion comprises a concave side, the concave side positioned to face the proximal end of the hysteroscope.

11. The method of claim 9 additionally comprising forming the at least one slit opening in the dome-shaped portion by cutting from the concave side.

12. The method of claim 1 wherein the removable outflow channel is configured so that the distal end of removable outflow channel cannot extend substantially beyond the distal end of the hysteroscope.

13. The method of claim 1, wherein the distal end of the removable outflow channel and the distal end of the hysteroscope are configured such that the respective distal ends form a flush distal tip surface.

14. The method of claim 1 wherein the removable outflow channel has an inner surface and an outer surface, and wherein the outer surface defines part of an inflow channel for introducing inflow fluid into the patient, and wherein the inner surface of the removable outflow channel defines the outflow channel lumen.

* * * * *